US011406812B2

(12) United States Patent
Agah et al.

(10) Patent No.: US 11,406,812 B2
(45) Date of Patent: Aug. 9, 2022

(54) METHODS AND SYSTEMS FOR DEPLOYMENT, CHARGING AND RETRIEVAL OF INTRACARDIAC PUMPS

(71) Applicants: Ramtin Agah, Menlo Park, CA (US); Kamran Najmabadi, Palo Alto, CA (US)

(72) Inventors: Ramtin Agah, Menlo Park, CA (US); Kamran Najmabadi, Palo Alto, CA (US)

(73) Assignee: Ramtin Agah, Menlo Park, CA (US)

( * ) Notice: Subject to any disclaimer, the term of this patent is extended or adjusted under 35 U.S.C. 154(b) by 690 days.

(21) Appl. No.: 16/087,079

(22) PCT Filed: Mar. 21, 2017

(86) PCT No.: PCT/US2017/023348
§ 371 (c)(1),
(2) Date: Sep. 20, 2018

(87) PCT Pub. No.: WO2017/165372
PCT Pub. Date: Sep. 28, 2017

(65) Prior Publication Data
US 2020/0324033 A1    Oct. 15, 2020

Related U.S. Application Data

(60) Provisional application No. 62/310,981, filed on Mar. 21, 2016.

(51) Int. Cl.
*A61M 60/165* (2021.01)
*A61M 60/139* (2021.01)
(Continued)

(52) U.S. Cl.
CPC ........ *A61M 60/135* (2021.01); *A61M 60/148* (2021.01); *A61M 60/871* (2021.01); *A61M 2205/8243* (2013.01)

(58) Field of Classification Search
CPC ............. A61M 60/135; A61M 60/148; A61M 60/205; A61M 60/422; A61M 1/3653;
(Continued)

(56) References Cited

U.S. PATENT DOCUMENTS

| 5,911,685 A | 6/1999 | Siess et al. |
| 6,530,876 B1 | 3/2003 | Spence |

(Continued)

FOREIGN PATENT DOCUMENTS

| EP | 0894505 B1 | 6/1998 |
| WO | WO2009/091965 A1 | 7/2009 |

(Continued)

OTHER PUBLICATIONS

El Feghaly, M. et al., "Endovascular retrieval of two migrated venous stents by means of balloon catheters," Journal of Vascular Surgery, vol. 28, No. 3 (Sep. 1998), 6 pages.
(Continued)

*Primary Examiner* — Jon Eric C Morales
(74) *Attorney, Agent, or Firm* — Shay Glenn LLP

(57) ABSTRACT

An apparatus includes an expandable member, a blood pump, and a set of struts. The expandable member is configured to transition from a collapsed configuration to an expanded configuration. The expandable member includes a set of flexible segments that form a tubular wall defining an interior volume. The flexible segments contact an inner surface of a blood vessel when the expandable member is in the expanded position. The expandable member includes a set of attachment portions. Each of the struts has a first end portion coupled to a housing of the blood pump. Each of the struts has a second end portion configured to be removably coupled to a corresponding attachment portion such that the blood pump can be removably coupled to the expandable (Continued)

member with at least a portion of the housing disposed within the interior volume of the expandable member.

25 Claims, 19 Drawing Sheets

(51) Int. Cl.
*A61M 60/295* (2021.01)
*A61M 60/135* (2021.01)
*A61M 60/148* (2021.01)
*A61M 60/871* (2021.01)

(58) Field of Classification Search
CPC ........ A61M 1/3659; A61M 2205/8206; A61M 2210/127; A61M 60/414; A61M 60/419; A61F 2/2475; A61F 2220/0016; A61F 2/86; A61F 2002/8486; A61B 5/6862; A61B 5/6876; A61B 5/6882
See application file for complete search history.

(56) References Cited

U.S. PATENT DOCUMENTS

| | | | |
|---|---|---|---|
| 6,911,041 | B1 | 6/2005 | Zscheeg |
| 7,144,364 | B2 | 12/2006 | Barbut et al. |
| 7,479,102 | B2 | 1/2009 | Jarvik |
| 8,562,509 | B2 | 10/2013 | Bates |
| 8,641,594 | B2 | 2/2014 | LaRose et al. |
| 8,690,749 | B1 | 4/2014 | Nunez |
| 8,840,539 | B2 | 9/2014 | Zilbershlag |
| 9,211,368 | B2 | 12/2015 | Wampler |
| 9,276,641 | B2 | 3/2016 | Hur et al. |
| 9,463,268 | B2 | 10/2016 | Spence |
| 9,545,468 | B2 | 1/2017 | Aboul-Hosn et al. |
| 9,561,314 | B2 | 2/2017 | Aboul-Hosn et al. |
| 9,585,991 | B2 | 3/2017 | Spence |
| 2006/0036127 | A1 | 2/2006 | Delgado, III |
| 2009/0112312 | A1 | 4/2009 | Larose et al. |
| 2010/0191035 | A1 | 7/2010 | Kang et al. |
| 2010/0249489 | A1 | 9/2010 | Jarvik |
| 2012/0041255 | A1 | 2/2012 | Delgado, III |
| 2012/0283820 | A1 | 11/2012 | Tseng et al. |
| 2013/0138205 | A1 | 5/2013 | Kushwaha et al. |
| 2014/0051908 | A1 | 2/2014 | Khanal et al. |
| 2014/0128659 | A1 | 5/2014 | Heuring et al. |
| 2015/0038770 | A1 | 2/2015 | Colella |
| 2015/0119633 | A1 | 4/2015 | Haselby et al. |
| 2016/0064952 | A1 | 3/2016 | Matsumoto et al. |

FOREIGN PATENT DOCUMENTS

| | | |
|---|---|---|
| WO | WO2014/179391 | 11/2014 |
| WO | WO2015/130768 | 9/2015 |

OTHER PUBLICATIONS

Feezor, Robert J. et al. "Duodenal perforation with an inferior vena cava filter: An unusual cause of abdominal pain," Journal of Vascular Surgery, 10.1067 (2001), 3 pages.

Mukku, Venkata et al., "Use of Impella Ventricular Assist Device in Patients with Severe Coronary Artery Disease Presenting with Cardiac Arrest," International Journal of Angiology, vol. 21, No. 3 (Aug. 20, 2012), 4 pages.

Terry-Cobo, Sarah. "VADovations develops blood pump," Innovation to Enterprise—online [retrieved on Sep. 19, 2018 from https://i2e.org/vadovations-develops-blood-pump/] (May 16, 2013), 2 pages.

Tsiouris, Athanasios et al. "Short and long term outcomes of 200 patients supported by continuous-flow left ventricular assist devices," World Journal of Cardiology, vol. 7, Issue 11 (Nov. 26, 2015), 10 pages.

International Search Report and Written Opinion for International Application No. PCT/US2017/023348, dated Jun. 7, 2017.

METHODS AND SYSTEMS FOR DEPLOYMENT, CHARGING AND RETRIEVAL OF INTRACARDIAC PUMPS

CROSS-REFERENCE TO RELATED APPLICATIONS

This application is a U.S. national stage filing under 35 U.S.C. § 371 of international Application No. PCT/US2017/023348, entitled "METHODS AND SYSTEMS FOR DEPLOYMENT, CHARGING AND RETRIEVAL OF INTRACARDIAC PUMPS," filed Mar. 21, 2017, which claims the benefit of priority to U.S. Provisional Application Ser. No. 62/310,981, entitled "Intracardiac Pump and Methods for Deployment and Charging," filed Mar. 21, 2016, the entire disclosure of each of which is incorporated herein by reference in its entirety.

BACKGROUND

The embodiments described herein relate to circulatory support systems and methods. More particularly, the embodiments described herein relate to ventricular assist devices that can be implanted and removed using endovascular procedures.

Known mechanical devices, such as left ventricle assist devices ("LVAD") or intra-aortic balloon pumps ("IABP") can be used to supplement the heart's pumping ability. LVADs are surgically implanted into the chest cavity and provide blood flow from left ventricle of the heart to the aorta. LVADs are often implanted in patients waiting for a heart transplant or as a temporary means to assist the patient in recovering from a temporary heart failure. In some instances, LVADs are implanted as a long-term solution for patients that are not eligible for a heart transplant. IABPs are catheter-based devices with a balloon that inflates inside the aorta when the aortic value is closed (i.e., during diastole) to force blood further into the circulatory system. These devices provide a temporary augmentation of the heart function via a balloon/pump internally connected to the driver outside the body via a catheter.

Although such circulatory-assist devices can effectively supplement the output of the heart, they are not without significant risks. For example, known methods for implanting LVADs require invasive surgical procedures. Specifically, some known methods of implanting LVADs involve open heart surgery (e.g., a midline sternotomy of the chest and utilization of cardiopulmonary bypass). Known methods of implanting circulatory assist devices often include surgical incisions into the heart, which may further weaken the heart. Moreover, because patients in need of a circulatory assist device are usually suffering from chronic congestive heart failure, they are often even more susceptible to complications during and after surgery. Accordingly, the survival rate for LVAD patients one year after implantation is only about 78 percent (Tsiouris et al., "Short and Long Term Outcomes of 200 Patients Supported by Continuous-Flow Left Ventricular Assist Devices," World J. Cardiology, Nov. 26, 2015).

In addition to surgical risks, known circulatory-assist devices include components, such as the pump, that are implanted within the patient's body, and components, such as the controller and power source, that remain outside of the patient's body. The internal and external components are connected using electrical leads or a "driveline" that extends from inside of the body to the external power supply. Such connections are susceptible to infection and can further complicate the use of LVADs as a long-term solution.

To reduce the surgical risks associated with circulatory-assist devices and LVADs, there have been some attempts made to deliver pumps endovascularly, but these also have significant disadvantages. For example, because of the difficulty in traversing the aortic arch, some known procedures including implanting a pump in the descending aorta. Including the inflow cannula downstream of the aortic arch, however, minimizes the effects of the circulatory-assist system on the caudal regions of the patient.

Some known designs and methods include placing a pump within a cage, for example, a structure similar to a vena cava filter, and advancing the pump into the ascending aorta. Such methods, however, employ cages having "hooks" or other single points of attachment to the vessel wall. Accordingly, such systems are susceptible to downstream migration, tipping, and perforating the vessel walls (see, e.g., Feezor et al., "Duodenal Perforation with an Inferior Vena Cava Filter: An Unusual Cause of Abdominal Pain," J. Vascular Surgery, 2002). Moreover, the added weight of suspending a pump within such systems will likely exacerbate such issues.

Moreover, there are no effective techniques for the removal of such implanted pumps using endovascular procedures. For example, the likelihood of effective removal of system that includes a hook or anchor point in direct contact with the vessel wall can decrease with time. Specifically, support systems in direct contact can be subject to endothelialization of the anchor points, which increases the risk of perforating the vessel wall during removal.

Thus, a need exists for improved intracardiac pump assemblies and methods for implantation and removal of intracardiac pump assemblies using endovascular procedures.

SUMMARY

Intracardiac pump assemblies and methods for their implantation and removal are described herein. In some embodiments, an apparatus includes an expandable member, a blood pump, and a set of struts. The expandable member is configured to transition from a collapsed configuration to an expanded configuration. The expandable member includes a set of flexible segments that form a tubular wall defining an interior volume. The flexible segments contact an inner surface of a blood vessel when the expandable member is in the expanded position. The expandable member includes a set of attachment portions. Each of the struts has a first end portion coupled to a housing of the blood pump. Each of the struts has a second end portion configured to be removably coupled to a corresponding attachment portion such that the blood pump can be removably coupled to the expandable member with at least a portion of the housing disposed within the interior volume of the expandable member.

In some embodiments, a method includes inserting into an entry blood vessel a retrieval sheath. The retrieval sheath is advanced through the entry blood vessel and to a target blood vessel. The retrieval sheath is then positioned about a proximal end portion of a blood pump from a blood pump assembly. The blood pump assembly includes the blood pump, an expandable member, and a set of struts. The expandable member includes a tubular wall in contact an inner surface of the target blood vessel and defining an interior volume. The expandable member includes a set of attachment portions. A first end portion of each strut is coupled to the blood pump, and a second end portion of each strut is coupled to a corresponding attachment portion such that at least a portion of the blood pump is within the interior volume of the expandable member and suspended within the target blood vessel. The method includes moving an end portion of the retrieval sheath distally relative to the blood pump to: A) remove the second end portion of each strut from its corresponding attachment portion, and B) place the blood pump and the set of struts within the retrieval sheath. The retrieval sheath, including the blood pump and the plurality of struts, is retracted from the target blood vessel.

DETAILED DESCRIPTION

Figure 2:
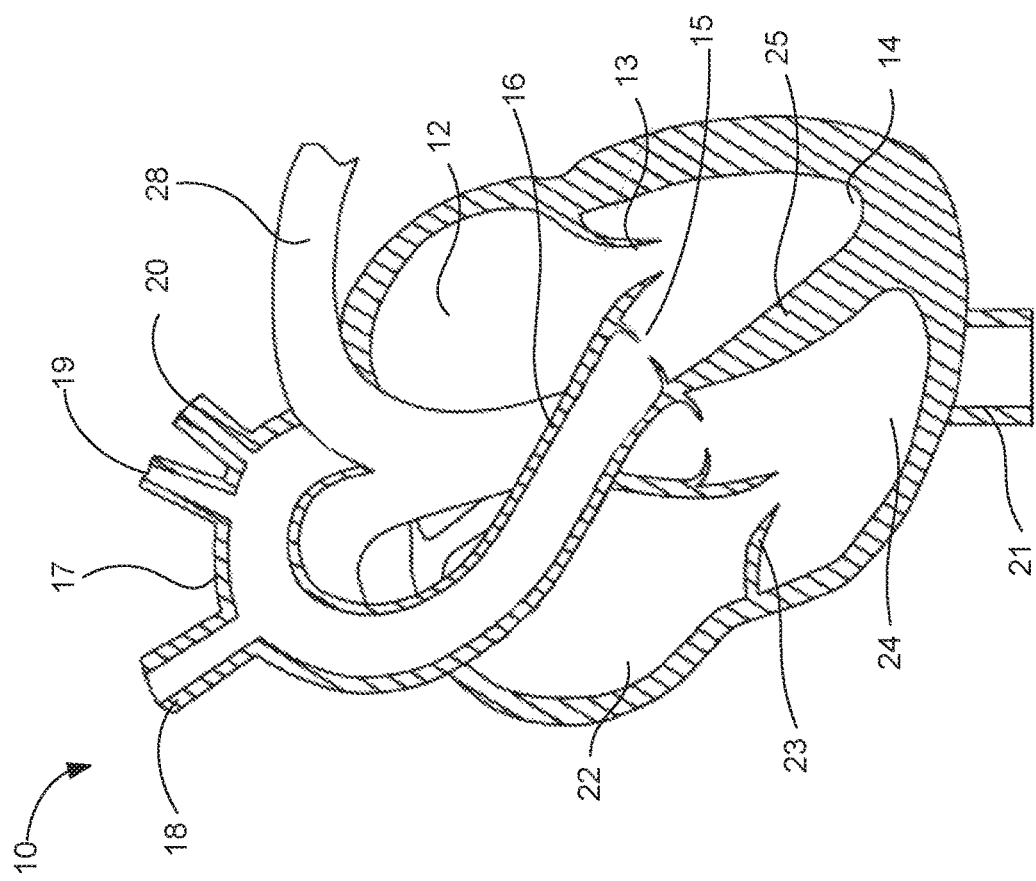
FIGS. 1 and 2 are cross-sectional schematics of the human heart.

Intracardiac pump assemblies and methods for their implantation and removal are described herein. In some embodiments, an apparatus includes an expandable member, a blood pump, and a set of struts. The expandable member is configured to transition from a collapsed configuration to an expanded configuration. The expandable member includes a set of flexible segments that form a tubular wall defining an interior volume. The flexible segments contact an inner surface of a blood vessel when the expandable member is in the expanded position. The expandable member includes a set of attachment portions. Each of the struts has a first end portion coupled to a housing of the blood pump. Each of the struts has a second end portion configured to be removably coupled to a corresponding attachment portion such that the blood pump can be removably coupled to the expandable member with at least a portion of the housing disposed within the interior volume of the expandable member.

In some embodiments, an apparatus includes an expandable member, a blood pump, a power supply, and a set of struts. The expandable member is configured to transition from a collapsed configuration to an expanded configuration. The expandable member including a set of flexible segments that form a tubular wall defining an interior volume. The flexible segments are configured to contact an inner surface of a blood vessel when the expandable member is in the expanded position. The expandable member includes a set of attachment portions. The power supply is coupled to the blood pump and is configured to provide power to drive the blood pump. Each of the struts has a first end portion coupled to at least one of the blood pump or the power supply. Each of the struts has a second end portion configured to be removably coupled to a corresponding attachment portion such that the blood pump and the power supply can be removably coupled to the expandable member with at least one of a portion of the blood pump or a portion of the power supply disposed within the interior volume of the expandable member.

In some embodiments, kit includes a blood pump assembly and a set of expandable members. The blood pump assembly includes a housing and a set of struts. Each strut has a first end portion coupled to the housing. Each of the expandable members is configured to transition from a collapsed configuration to an expanded configuration. Each of the expandable members includes a set of flexible segments that form a tubular wall defining an interior volume. The flexible segments are configured to contact an inner surface of a blood vessel when the expandable member is in the expanded position. Each of the expandable members includes a plurality of attachment portions. Each of the struts has a second end portion configured to be removably coupled to a corresponding attachment portion of each expandable member such that the blood pump can be removably coupled to each expandable member with at least a portion of the housing disposed within the interior volume of the expandable member. The set of expandable members includes a first expandable member having a first size and a second expandable member having a second size. The first size is different than the second size.

In some embodiments, a method of implanting a blood pump assembly includes inserting into an entry blood vessel the blood pump assembly. The blood pump assembly includes a blood pump, an expandable member, and a set of struts. The expandable member includes a set of flexible segments that form a tubular wall defining an interior volume. The expandable member includes a set of attachment portions. A first end portion of each strut is coupled to the blood pump. A second end portion of each strut is removably coupled to a corresponding attachment portion such that at least a portion of the blood pump is within the interior volume of the expandable member. The inserting is performed when the expandable member is in a collapsed configuration. The blood pump assembly is advanced through the entry blood vessel and to a target blood vessel. The expandable member is then transitioned from the collapsed configuration to an expanded configuration such that the flexible segments contact an inner surface of the target blood vessel and the blood pump is suspended within the target blood vessel by the struts. The blood pump and the set of struts are configured to be removed from the target blood vessel by removing the second end portion of each strut from its corresponding attachment portion.

In some embodiments, a method includes inserting into an entry blood vessel a retrieval sheath. The retrieval sheath is advanced through the entry blood vessel and to a target blood vessel. The retrieval sheath is then positioned about a proximal end portion of a blood pump from a blood pump assembly. The blood pump assembly includes the blood pump, an expandable member, and a set of struts. The expandable member includes a tubular wall in contact an inner surface of the target blood vessel and defining an interior volume. The expandable member includes a set of attachment portions. A first end portion of each strut is coupled to the blood pump, and a second end portion of each strut is coupled to a corresponding attachment portion such that at least a portion of the blood pump is within the interior volume of the expandable member and suspended within the target blood vessel. The method includes moving an end portion of the retrieval sheath distally relative to the blood pump to: A) remove the second end portion of each strut from its corresponding attachment portion, and B) place the blood pump and the set of struts within the retrieval sheath. The retrieval sheath, including the blood pump and the plurality of struts, is retracted from the target blood vessel.

In some embodiments, a method includes inserting into an entry blood vessel a blood pump assembly that includes a blood pump, an inflow cannula, and an electrical lead. The blood pump assembly is advanced through the entry blood vessel and to an ascending aorta. The blood pump assembly is then affixed within the ascending aorta such that the inflow cannula is disposed through an aortic valve and within a left ventricle. The method further includes advancing a catheter through a superior vena cava and transseptally into the left ventricle. A proximal end portion of the electrical lead is captured, and a distal end portion of the lead is configured to be coupled to the blood pump. The proximal end portion of the electrical lead is retrieved through the superior vena cava, and is attached to a power supply located in a subcutaneous region of a body.

In some embodiments, a method includes inserting into an entry blood vessel a blood pump assembly that includes a blood pump and an inflow cannula. The blood pump assembly is advanced through the entry blood vessel and to an ascending aorta. The blood pump assembly is then affixed within the ascending aorta such that the inflow cannula is disposed through an aortic valve and within a left ventricle. The method further includes advancing a distal end portion of an electrical lead through a superior vena cava and transseptally into the left ventricle. The distal end portion of the lead is coupled to the blood pump. A proximal end portion of the electrical lead is configured to be coupled to a power supply located in a subcutaneous region of a body.

The term "about" when used in connection with a referenced numeric indication means the referenced numeric indication plus or minus up to 10 percent of that referenced numeric indication. For example, "about 100" means from 90 to 110.

The term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10 percent of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used in this specification and the appended claims, the words "proximal" and "distal" refer to direction closer to and away from, respectively, an operator of the medical device or implant. Thus, for example, the end of an implant first contacting the patient's body (i.e., furthest away from the practitioner implanting the device) would be the distal end of the implant, while the end opposite the distal end would be the proximal end of the implant.

As used herein, the terms "blood vessel" or "vessel" include any structure within the body through which blood can flow to tissues and organs within the body, including any vein, artery, or capillary. For example, the term "blood vessel" can refer to a subclavian vein, a femoral artery, an ascending aorta, or any other structure within the human body.

Figure 1:
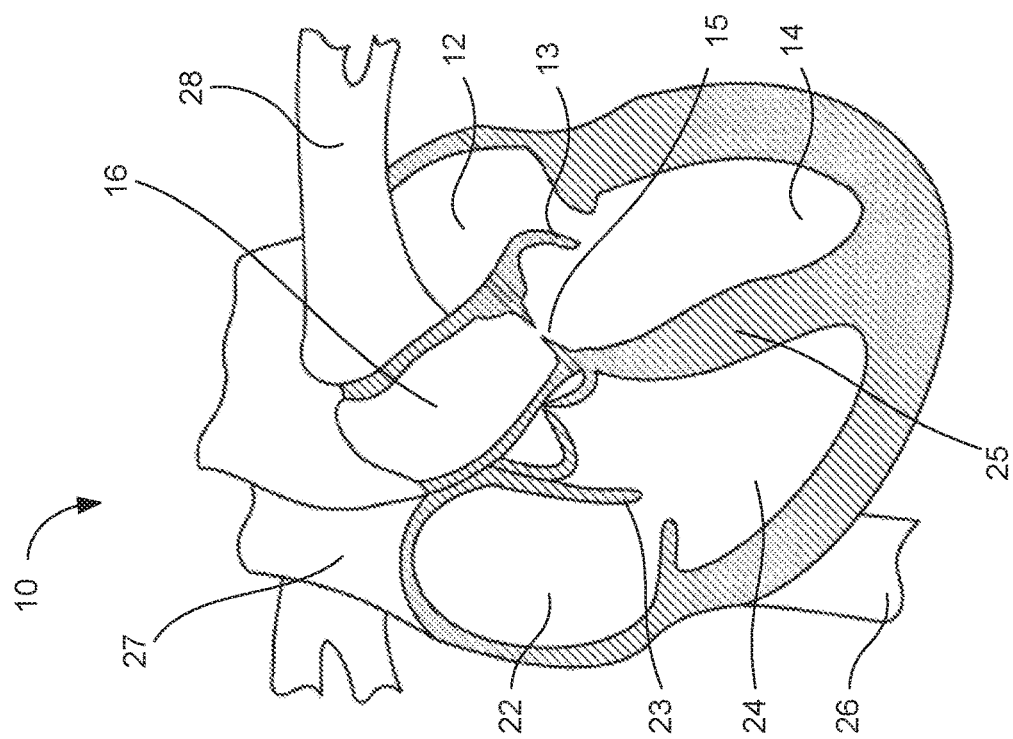

For reference, FIGS. 1 and 2 show various cross-sectional views of a human heart 10, which is an organ that pumps blood through the body via the circulatory system. The blood provides oxygen and nutrients to the tissues and removes carbon dioxide and other wastes. The heart 10 has four chambers: two upper chambers (the left atrium 12 and the right atrium 22) and two lower chambers (the left ventricle 14 and the right ventricle 24). The right atrium 22 and the right ventricle 24 together make up the right heart and the left atrium 12 and left ventricle 14 make up the left heart. A wall of muscle called the septum 25 separates the two sides of the heart.

The heart has multiple valves that separate the chambers of the heart, and control the flow of blood through the various blood vessels through which blood flows into and out of the heart 10. Specifically, the tricuspid valve 23 separates the right ventricle 22 from the right atrium 24. Blood flows from the superior vena cava 27 and the inferior vena cava 26 and into the right atrium 22. During diastole, the pressure in the ventricles drops, thus allowing the blood to flow from the right atrium 22 through the tricuspid valve 23 and into the right ventricle 24. During systole, blood flows out of the right ventricle 24 and into the pulmonary arteries (the left pulmonary artery 28 is identified in FIGS. 1 and 2).

The mitral valve 13 separates the left ventricle 12 from the left atrium 14. Oxygenated blood flows from the pulmonary veins and into the left atrium 12. During diastole, the pressure in the ventricles drops, thus allowing the blood to flow from the left atrium 12 through the mitral valve 13 and into the left ventricle 24. During systole, blood flows out of the left ventricle 14, through the aortic valve 15 and into the aorta. The aorta includes the ascending aorta 16, the aortic arch 17, and the descending aorta 21 (see FIG. 2). The aortic arch 17 supplies blood to the brachiocephalic artery 18, the left common carotid artery 19 and the left subclavian artery 20. Heartstrings (chordae tendinae) anchor the valves to the heart muscles. The sinoatrial nodes produce the electrical pulses that drive the heart contractions.

Figure 6:
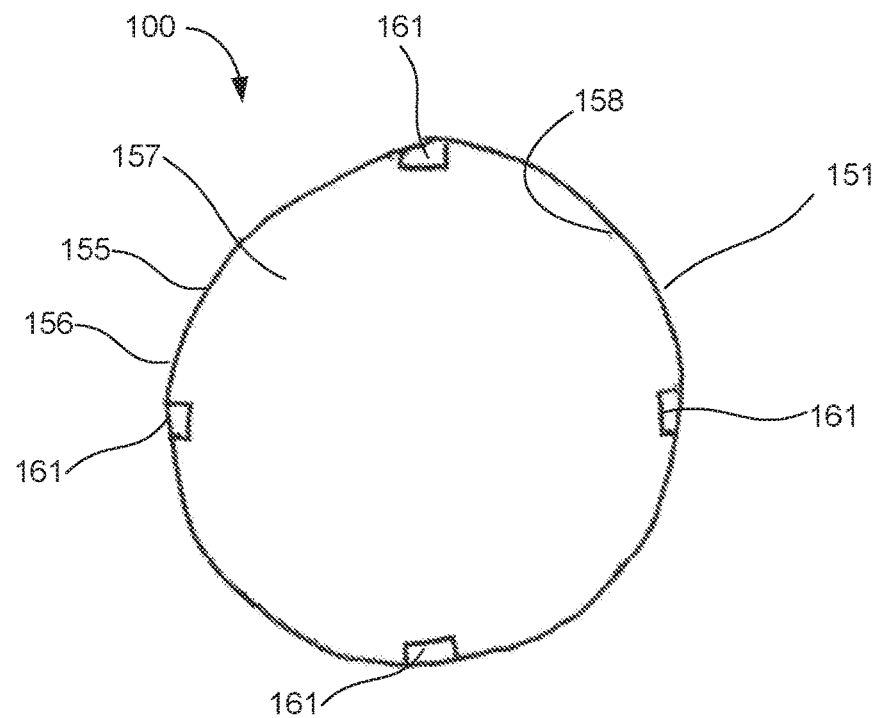

FIGS. 3-6 are schematic illustrations of a blood pump assembly 100, according to an embodiment. The blood pump assembly 100 is shown in a first configuration (FIG. 3), a second configuration (FIGS. 4 and 5) and a third configuration (FIG. 6). The blood pump assembly 100 includes a blood pump 101, a set of struts 131, and an expandable member 151. The blood pump 101 can be any suitable device that pumps blood and provides the desired flow characteristics to supplement the output of the heart. For example, the blood pump 101 (and any of the blood pumps described herein) includes a pumping unit (not shown, e.g., an impeller, a roller, a balloon, or the like) enclosed within a housing 103. The blood pump 101 produces any suitable blood flow rate, for example a flow rate of between 0.5 liters per minute and 3 liters per minute. In some embodiments, the blood pump 101 (or any of the blood pumps described herein) can produce a flow rate of between 1.0 liters per minute and 2.5 liters per minute. Moreover, the blood pump 101 (and any of the blood pumps described herein) can be configured to limit the amount of heat transfer into the blood, reduce and/or eliminate points of stasis, or the like. In some embodiments, the blood pump 101 can include a miniature axial heart pump. In some embodiments, the blood pump 101 (and any of the blood pumps described herein) can include a miniature pump similar to those developed by VADovations, Inc., and disclosed in U.S. Pat. No. 9,211,368, entitled "Heart Assist Device," which is incorporated herein by reference in its entirety. In some embodiments, the assembly 100 can include a power supply (not shown) that is close-coupled to the blood pump 101. Similarly stated, in some embodiments the assembly 100 (or any of the assemblies described herein) can include a power supply (battery, capacitance power supply, etc.) that can be disposed along with the blood pump 101 within the vasculature. In such embodiments, the assembly 100 (or any of the assemblies described herein) can also include a wireless charging system of the types shown and described herein (e.g., the wireless systems 781, 800).

The expandable member 151 is configured to transition from a collapsed configuration (FIG. 3) to an expanded configuration (FIGS. 4-6), and includes a series of flexible segments 152. The flexible segments 152 can be coupled together in any suitable pattern to form a tubular wall 155 having an outer surface 156 and an inner surface 158, and that defines an interior volume 157. The expandable member 151 can include any suitable number of flexible segments 152 in any suitable form, such as coiled members, longitudinal members, or the like. For example, in some embodiments, the flexible segments 152 can be braided or woven to produce the tubular wall 155 that can transition from the collapsed configuration to the expanded configuration. In some embodiments, the expandable member 151 can include multiple layers of flexible segments to produce the desired spring characteristics and strength. In yet other embodiments, the flexible segments 152 can be produced from a monolithic sheet of material (e.g., by a laser cutting process). Moreover, any the tubular wall 155 (and any of the tubular walls described herein) can have any suitable pore size (or arrangement of openings) so that the outer surface 156 provides the desired contact area within the bodily lumen. In this manner, as described herein, the expandable member 151 can be resistant to migration and can provide support for the blood pump 101 suspended within the interior volume 157.

The expandable member 151 and the flexible segments 152 (and any of the expandable members described herein) can be constructed from any suitable material that provides the desired strength, spring characteristics and biocompatibility. For example, in some embodiments. The expandable member 151 (and any of the expandable members described herein) can be constructed from a metal, such as, for example, a medical grade stainless steel, a cobalt-based alloy, platinum, gold, titanium, tantalum, and/or niobium. In some embodiments, the expandable member 151 (and any of the expandable members described herein) can be constructed from a shape memory material, such as a nickel-titanium alloy (e.g., Nitinol®). In other embodiments, the expandable member 151 (and any of the expandable members described herein) can be constructed from a polymeric material, such as, for example, poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), poly(phosphate ester), or the like.

Figure 4:
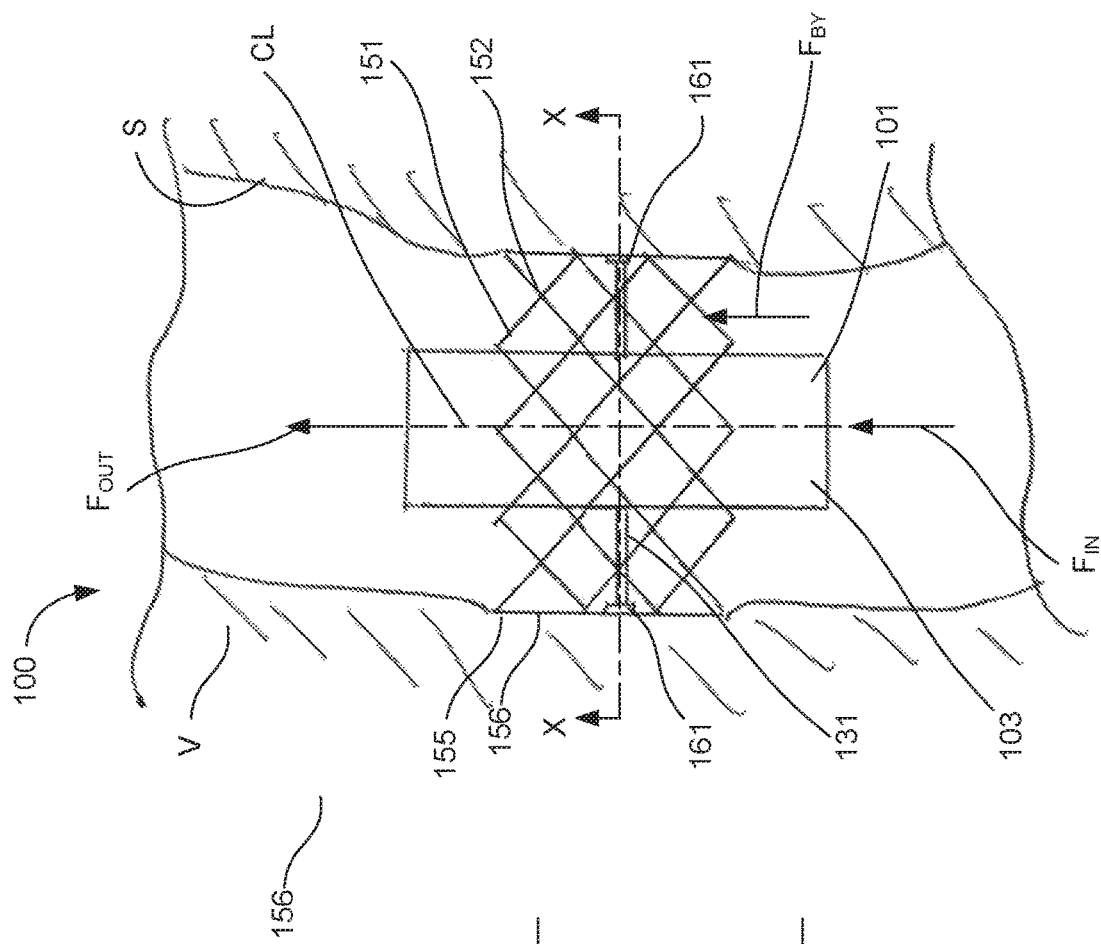
FIGS. 3 and 4 are schematic illustrations of a blood pump assembly, according to an embodiment, in a first configuration and a second configuration, respectively.

As shown in FIG. 4, when the blood pump assembly 100 is deployed within a blood vessel V and the expandable member 151 is in its expanded configuration, the outer surface 156 of the tubular wall 155 is in contact with the inner surface S of the blood vessel V. The expandable member 151 is sized and configured such that the outer surface 156 exerts a radially outward force on the inner surface S to maintain (or anchor) the expandable member 151 within the blood vessel. By providing the anchoring force circumferentially and along the axial length $L_C$ of the expandable member 151 (as opposed to multiple, discrete anchor points), the expandable member 151 and the blood pump assembly 100 are resistant to migration (i.e., movement along the longitudinal center line CL) within the blood vessel V. Similarly stated, the expandable member 151 distributes the radially outward anchoring force over the contact area of the outer surface 156, thereby minimizing migration. This arrangement also minimizes and/or eliminates tipping (i.e., rotation about an axis non-parallel to the longitudinal center line CL). Moreover, by avoiding anchoring via discrete anchor points, the expandable member 151 and the blood pump assembly 100 reduces the likelihood of perforating the wall of the blood vessel V.

Figure 3:
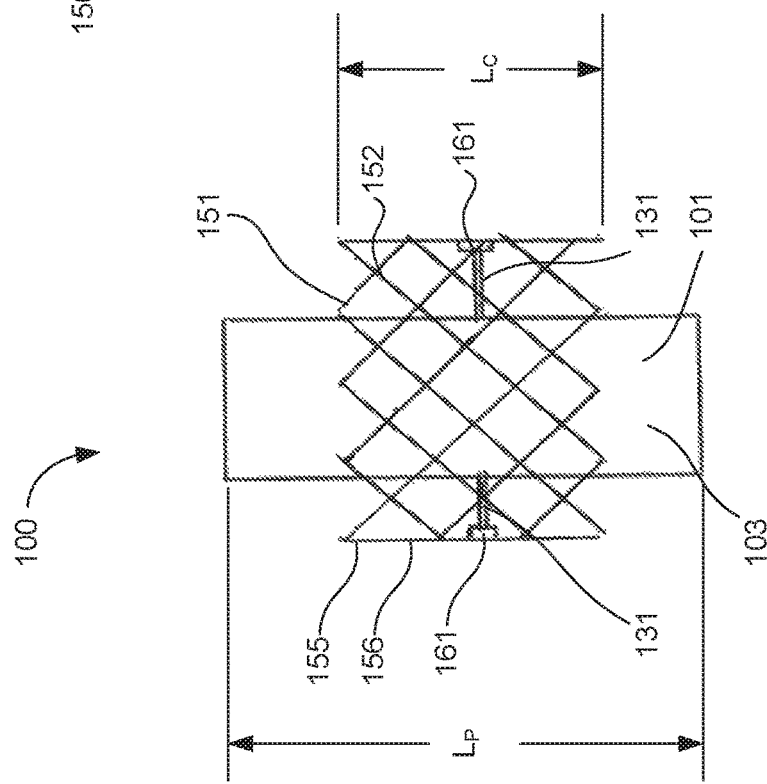
Figure 5:
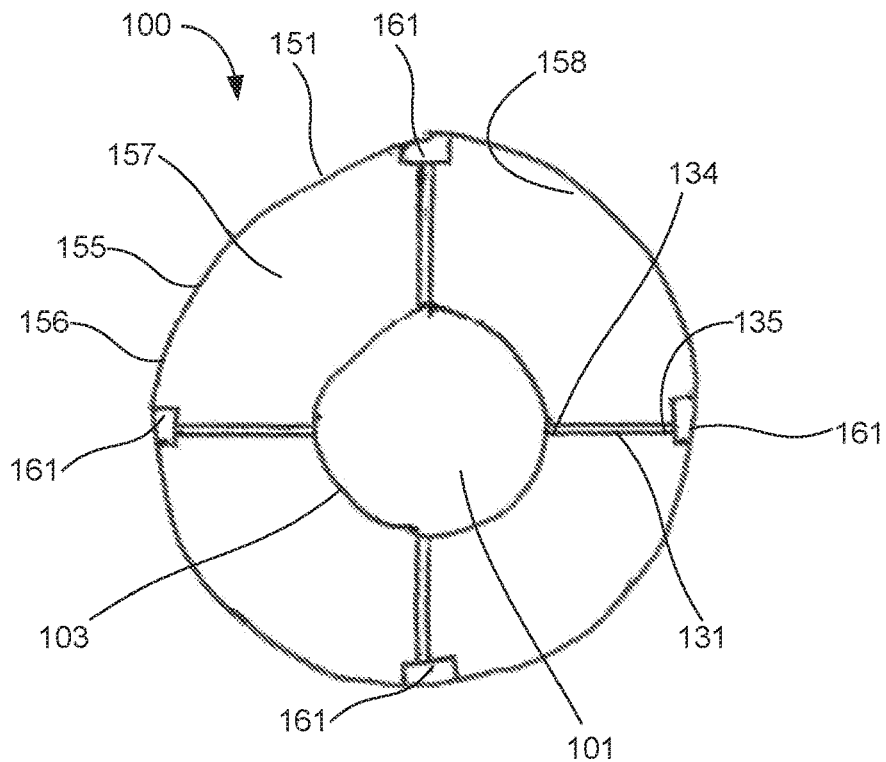
FIGS. 5 and 6 are cross-sectional views of the blood pump assembly taken along line X-X in FIG. 4 in the second configuration, and a third configuration, respectively.

Referring to FIG. 3, the expandable member 151 has a contact length $L_C$ over which the outer surface 156 of the tubular wall 155 is in contact with the inner surface S of the blood vessel V. The contact length $L_C$ can be any suitable distance to provide the desired anchoring and/or stability characteristics. For example, in some embodiments, the contact length $L_C$ can be equal to or greater than a length $L_P$ of the blood pump 101. In other embodiments, the contact length $L_C$ can be less than a length $L_P$ of the blood pump 101. For example, in some embodiments, the contact length $L_C$ can be at least about one quarter of the length $L_P$ of the blood pump 101. In some embodiments, the contact length $L_C$ can be less than about three quarters of the length $L_P$ of the blood pump 101. In some embodiments, the contact length $L_C$ can be less than about half of the length $L_P$ of the blood pump 101. In some embodiments, the contact length $L_C$ can be less than about one quarter of the length $L_P$ of the blood pump 101.

The expandable member 151 includes a series of attachment portions 161 to which a corresponding strut 131 can be removably and/or releasably coupled. In some embodiments, the attachment portions 161 (and any of the attachment portions described herein) can be a separate structure or mechanism that is coupled to the flexible segments 152 or tubular wall 155. In other embodiments, the attachment portions 161 (and any of the attachment portions described herein) can be monolithically constructed with (or a portion of) the flexible segments 152 or tubular wall 155. Although the expandable member 151 is shown as including four attachment portions 161, in other embodiments, the expandable member 151 (and any of the expandable members described herein) can include any suitable number of attachment portions (e.g., between two and eight, between two and ten, or between two and 12). Although the attachment portions 161 are shown as extending within the internal volume 157, in other embodiments, the attachment portions 161 can be flush with the inner surface 158 of the tubular wall 155. Similarly stated, in some embodiments, the tubular wall 155 and the set of attachment portions 161 define a continuous inner surface 158.

The blood pump assembly 100 includes a set of struts 131. Each strut 131 includes a first end portion 134 and a second end portion 135. The first end portion 134 of each strut 131 is coupled to the pump 101. More particularly, the first end portion 134 of each strut 131 is coupled to the housing 103 of the pump 101. The first end portion 134 can be coupled to the housing 103 in any suitable manner. For example, in some embodiments, the first end portion 134 can be coupled by a pin joint or a ball joint, such that the strut 131 can rotate relative to the housing (e.g., when the expandable member 151 moves from its collapsed configuration to its expanded configuration). In other embodiments, the first end portion 134 can be coupled to the housing 103 by a band, weld joint, or adhesive. The second end portion 135 of each strut is removably coupled to its corresponding attachment portion 161 of the expandable member 151. In this manner, the blood pump 101 can be removably coupled to the expandable member 151 by the set of struts 131. More particularly, the blood pump 101 can be coupled to the expandable member 151 with at least a portion of the housing 103 disposed within the interior volume 157 of the expandable member 151. Similarly stated, when the blood pump assembly 100 is in its first configuration and its second configuration, the blood pump 101 is suspended within the interior volume 157 by the set of struts 131.

Because the second end portion 135 of each strut is removably (or releasably) coupled to the corresponding attachment portion 161, the blood pump 101 and the struts 131 can be removed from the expandable member 151. This arrangement allows the blood pump assembly 100 to be moved from the second configuration (FIGS. 4 and 5) to the third configuration (FIG. 6). In this manner, the blood pump 101 and the struts 131 can be removed when the assembly 100 is within the body, for example, if the patient no longer needs the pump assembly 100, if the blood pump 101 has malfunctioned, or the like. Moreover, as described in more detail below, the blood pump 101 and the struts 131 can be removed endovascularly by decoupling (or releasing) the struts 131 from the attachment portions 161.

The struts 131 can be constructed from any suitable material that provides the desired strength to suspend the blood pump 101 within the blood vessel V. Moreover, the struts 131 are flexible and can change their length and/or orientation to allow the expandable member to transition from the collapsed configuration to the expanded configuration. For example, in some embodiments, the struts 131 can be constructed from a metallic material, such as, a medical grade stainless steel. In other embodiments, the struts 131 (and any of the struts described herein) can be constructed from a shape memory material, such as a nickel-titanium alloy (e.g., Nitinol®). In other embodiments, the struts 131 (and any of the struts described herein) can be constructed from a polymeric material, such as, for example, poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), poly (phosphate ester), or the like.

In some embodiments, either of the attachment portions 161 or the second end portion 135 of the struts 131 can include a latch, a locking mechanism, or detent that maintains the struts 131 within the attachment portions 161 until a retrieval force threshold has been exceeded. This arrangement prevents the struts 131 from being inadvertently released or removed from the expandable member 151.

Although the blood pump assembly 100 is shown as including four struts 131, in other embodiments, the blood pump assembly 100 (and any of the blood pump assemblies described herein) can include any suitable number of struts (e.g., between two and eight, between two and ten, or between two and 12).

In use, the blood pump assembly 100 (and any of the blood pump assemblies described herein) can be implanted into a patient's circulatory system to supplement the blood flow output of the heart. Because the blood pump 101 and the struts 131 can be removed from the expandable member 151, the blood pump assembly 100 (and any of the blood pump assemblies described herein) is well suited for both short term and long term use. For example, the blood pump assembly 100 (and any of the blood pump assemblies described herein) can be implanted, and then removed within ten days, one month, two months, or less than one year when the patient no longer needs the circulatory assistance. As described herein, the blood pump 101 and the struts 131 can be removed (leaving the expandable member 151 behind) without obstructing the blood vessel. Similarly, when implanted for long-term use (e.g., one year, two years, or longer), the blood pump 101 and the struts 131 can be removed when there is a failure of the blood pump 101, to replace the batteries (not shown) or the like.

To implant the blood pump assembly 100, the assembly 100 is first inserted into an entry blood vessel (e.g., the femoral artery) endovascularly. Similarly stated, the assembly 100 is first inserted into an entry blood vessel (e.g., the femoral artery) using percutaneous and/or minimally invasive techniques. The blood pump assembly 100 is inserted when in its first (or collapsed) configuration, as shown in FIG. 3. The blood pump assembly 100 is then advanced to a target blood vessel (identified as the blood vessel V in FIG. 4). The target blood vessel V can be any suitable blood vessel, such as the descending aorta, the aortic arch, or the ascending aorta. The blood pump assembly 100 is then transitioned from its first (or collapsed) configuration to its second (or expanded configuration). When in the expanded configuration, the outer surface 156 of the tubular wall 155 contacts, engages and/or exerts a radially outward force upon the inner surface S of the blood vessel V, as described above. In this manner, the blood pump assembly 100 can be anchored in the desired location within the blood vessel V.

After being implanted, the blood pump 101 can be actuated (or powered) to supplement the blood flow provided by the patient's heart. In particular, the blood pump 101 (and any of the blood pumps described herein) can supplement the blood flow continuously or only during diastole. As shown in FIG. 4, the blood pump 101 can receive an inlet blood flow $F_{IN}$ (e.g., via an inlet cannula, not shown) and produce an outlet blood flow $F_{OUT}$. Because the blood pump 101 is suspended with the blood vessel V, the blood flow produced by the heart (e.g., during systole) can flow around the blood pump 101, as shown by the arrow $F_{BY}$.

When removal of the blood pump 101 is desired, the struts 131 can be detached from attachment portions 161 of the expandable member 151, and the blood pump 101 and the struts 131 can be removed, as shown in FIG. 6. This can be accomplished using any tools or by any of the methods described herein. In this manner, the only structure left in the blood vessel V is the expandable member 151, which does not block the blood vessel V. By removing the struts 131 from the expandable member 151, as opposed to removing the end portion of the struts 131 directly from the inner surface S of the blood vessel, the risk of perforation or tearing of the blood vessel V is minimized Specifically, because implanted structure that is in direct contact with the inner surface S may be subject to tissue ingrowth, endothelialization, or the like, the arrangement of the assembly 100 provides a reliable way to remove the blood pump 101 via endovascular techniques and with minimal risk of damaging the blood vessel V.

Figure 7:
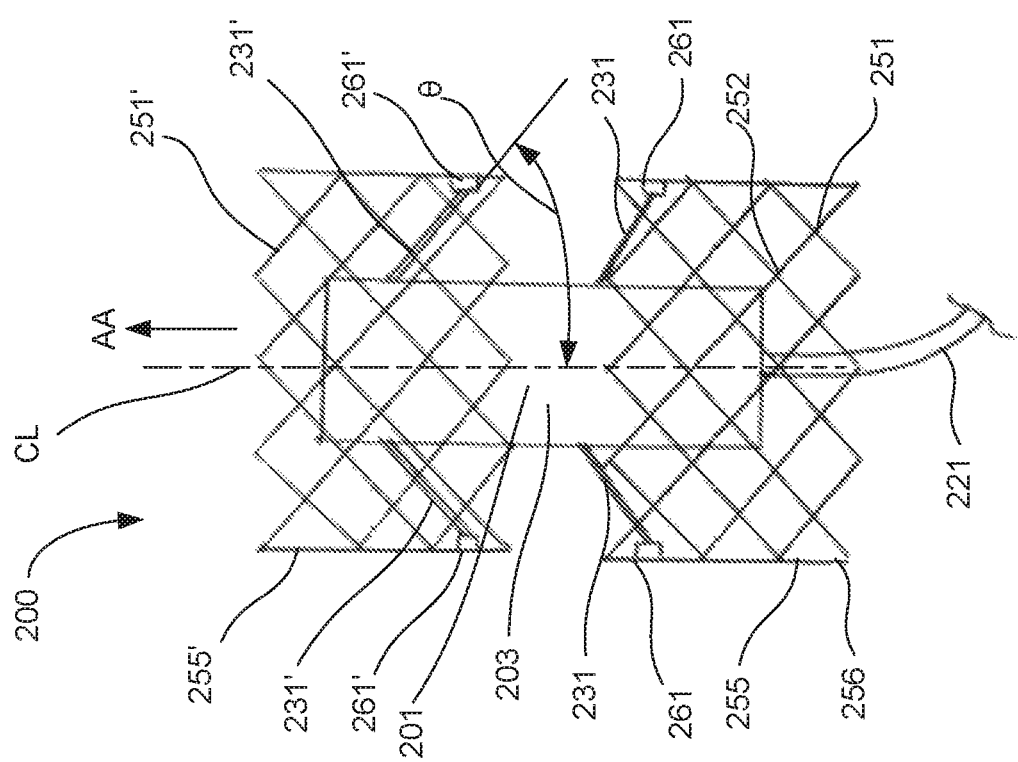
FIG. 7 is a schematic illustration of a blood pump assembly, according to an embodiment.

Although the blood pump assembly 100 is shown as including one expandable member 151, in other embodiments any of the blood pump assemblies described herein can include any number of expandable members that are removably coupled to a blood pump, a power supply or a set of struts. In this manner, the expandable assemblies can be positioned about the blood pump and/or power supply to produce the desired stability of the system (e.g., to minimize migration, tipping or the like). For example, FIG. 7 is a schematic illustration of a blood pump assembly 200, according to an embodiment. Like the blood pump assemblies 100 and 400, the blood pump assembly 200 can be transitioned between a first configuration (collapsed), a second configuration (expanded deployed) and a third configuration (pump retrieved). The blood pump assembly 200 includes a blood pump 201, two sets of struts 231, 231', and two expandable members 251, 251'. The blood pump 201 can be any suitable device that pumps blood and provides the desired flow characteristics to supplement the output of the heart. For example, the blood pump 201 (and any of the blood pumps described herein) includes a pumping unit (not shown, e.g., an impeller, a roller, a balloon, or the like) enclosed within a housing 203. An inflow cannula 221 is coupled to the distal end portion of the housing 203, and the blood pump 201 produces an output flow in the direction indicated by the arrow AA in FIG. 7. The blood pump 201 produces any suitable blood flow rate, for example a flow rate of between 0.5 liters per minute and 3 liters per minute. In some embodiments, the blood pump 201 (or any of the blood pumps described herein) can produce a flow rate of between 1.0 liters per minute and 2.5 liters per minute. Moreover, the blood pump 201 (and any of the blood pumps described herein) can be configured to limit the amount of heat transfer into the blood, reduce and/or eliminate points of stasis, or the like.

In some embodiments, the assembly 200 can include a power supply (not shown) that is also disposed within the housing 203. In this manner, the assembly 200 (or any of the assemblies described herein) can include a power supply (battery, capacitance power supply, etc.) that can be disposed along with the blood pump 201 within the vasculature. In such embodiments, the assembly 200 (or any of the assemblies described herein) can also include a wireless charging system of the types shown and described herein (e.g., the wireless systems 781, 800).

The first expandable member 251 is coupled to the distal end portion of the housing 203, and is configured to transition from a collapsed configuration to an expanded configuration. The first expandable member 251 includes a series of flexible segments 252 coupled together in any suitable pattern to form a tubular wall 255 having an outer surface 256 and an inner surface, and that defines an interior volume. The second expandable member 251' is coupled to the proximal end portion of the housing 203, and is configured to transition from a collapsed configuration to an expanded configuration. Like the first expandable member 251, the second expandable member 251' includes a series of flexible segments coupled together in any suitable pattern to form a tubular wall 255' having an outer surface and an inner surface, and that defines an interior volume.

The expandable members 251, 251' can include any suitable number of flexible segments (e.g., the flexible segments 252) in any suitable form, such as coiled members, longitudinal members, or the like. For example, in some embodiments, the flexible segments can be braided or woven to produce the tubular wall that can transition from the collapsed configuration to the expanded configuration. In some embodiments, the expandable member can include multiple layers of flexible segments to produce the desired spring characteristics and strength. In yet other embodiments, the flexible segments can be produced from a monolithic sheet of material (e.g., by a laser cutting process). Moreover, any the tubular walls 255, 255' (and any of the tubular walls described herein) can have any suitable pore size (or arrangement of openings) so that the outer surface provides the desired contact area within the bodily lumen, as described herein. In this manner, as described herein, the expandable members 251, 251' can be resistant to migration and can provide support for the blood pump 201 (and any power supply coupled within the housing 203).

When in the expanded configuration, first expandable member 251 is spaced apart from the second expandable member 251'. In this manner, the overall length of contact between the outer surfaces of the expandable members is greater than the sum of the contact length of each of the expandable members. As shown, the overall contact length (i.e., the length along the axial centerline CL from the distal-most portion of the first expandable member 251 to the proximal-most portion of the second expandable member 251') is greater than the length of the pump 201 and/or the pump housing 203. In this manner, the "two expandable member configuration" of the assembly 200 provides the desired anchoring and/or stability characteristics. For example, in some embodiments, a ratio between the overall contact length and the length of the blood pump 201 can be at least about 1.2, 1.4, 1.6, 1.8 or 2.0. The overall length can be limited by, for example, the flexibility to advance the blood pump assembly 200 within the vasculature of the patient (e.g., through the aortic arch) using endovascular techniques, as described herein. In other embodiments, the overall contact length can be less than the length of the blood pump 201. For example, in some embodiments, a ratio between the overall contact length and the length of the blood pump 201 can be at least about 0.6, 0.8, or 0.9.

When the blood pump assembly 200 is deployed within a blood vessel (not shown) and the expandable members 251, 251' are in their expanded configurations, the outer surfaces of the tubular walls 255, 255' can contact the inner surface of the blood vessel to maintain (or anchor) the expandable members 251, 251' within the blood vessel. By providing the anchoring force circumferentially and along the axial length of each expandable member 251, 251', as well as the overall contact length, the blood pump assembly 200 is resistant to migration (i.e., movement along the longitudinal center line CL) within the blood vessel. Similarly stated, the expandable members 251, 251' distribute the radially outward anchoring force over the contact area of the outer surfaces of each expandable member, thereby minimizing migration. This arrangement also minimizes and/or eliminates tipping (i.e., rotation about an axis non-parallel to the longitudinal center line CL). Moreover, by avoiding anchoring via discrete anchor points, the expandable member 251 and the blood pump assembly 200 reduces the likelihood of perforating the wall of the blood vessel.

The first expandable member 251 and the second expandable member 251' each include a series of attachment portions 261, 261' to which a corresponding strut 231, 231' can be removably and/or releasably coupled. In some embodiments, the attachment portions 261, 261' (and any of the attachment portions described herein) can be a separate structure or mechanism that is coupled to the flexible segments or tubular wall 255, 255' of each expandable member. In other embodiments, the attachment portions 261, 261' (and any of the attachment portions described herein) can be monolithically constructed with (or a portion of) their respective flexible segments or tubular wall. Although the expandable members 251, 251' are shown as including two attachment portions 261, 261', in other embodiments, the expandable members 251, 251' (and any of the expandable members described herein) can include any suitable number of attachment portions (e.g., between two and eight, between two and ten, or between two and 12). Although the attachment portions 261, 261' are shown as extending within the internal volume, in other embodiments, the attachment portions 261, 261' can be flush with the inner surface of the tubular walls 255, 255'. Similarly stated, in some embodiments, the tubular walls 255, 255' and the respective set of attachment portions 261, 261' define a continuous inner surface.

The blood pump assembly 200 includes two sets of struts 231, 231'. The first set of struts 231 correspond to the first expandable member 251 and the second set of struts 231' correspond to the second expandable member 251'. Each strut 231, 231' includes a first end portion and a second end portion. The first end portion of each strut 231, 231' is coupled to the pump 201 and/or the housing 203. The first end portion can be coupled to the housing 203 in any suitable manner, such as a pin joint or a ball joint. In this manner, the struts 231, 231' can rotate or otherwise move relative to the housing (e.g., when the expandable members 251, 251' move from their collapsed configuration to their expanded configuration). In other embodiments, the first end portion of each strut can be coupled to the housing 203 by a band, weld joint, or adhesive. As shown, the struts 231, 231' are coupled to the housing 203 such that a longitudinal axis of the strut forms an acute strut angle θ with the axial centerline CL of the housing 203 (measured from the distal-most end of the axial centerline CL). Although the strut angle θ can change when the expandable members 251, 251' transition from their collapsed configuration to their expanded configuration, maintain the strut angle within a desired range can facilitate removal and/or collapsing of the struts during the removal process, as described herein. Although the strut angle θ is shown as being acute for both the first set of struts 231 and the second set of struts 231', in other embodiments, the strut angle of the first set of struts 231 can be different than the strut angle of the second set of struts 231'. For example, in some embodiments, the strut angle of the first set of struts 231 can be obtuse and the strut angle of the second set of struts 231' can be acute. In other embodiments, the strut angle of the first set of struts 231 can be acute and the strut angle of the second set of struts 231' can be obtuse. In yet other embodiments, the strut angle of the first set of struts 231 and the strut angle of the second set of struts 231' can both be obtuse.

The second end portion of each strut 231, 231' is removably coupled to its corresponding attachment portion 261, 261'. In this manner, the blood pump 201 (and/or the power supply therein) can be removably coupled to the expandable members 251, 251' by the two sets of struts 231 231'. Similarly stated, when the blood pump assembly 200 is in its first configuration and its second configuration, the blood pump 201 is suspended within the interior volume of the expandable members 251, 251' by the two sets of struts 231, 231'. Because the second end portion of each strut is removably (or releasably) coupled to the corresponding attachment portion, the blood pump 201 and the struts 231, 231' can be removed from the expandable members 251, 251' by any of the methods described herein.

In some embodiments, either of the attachment portions 261, 261' or the struts 231, 231' can include a latch, a locking mechanism, or detent that maintains the struts 231, 231' within the attachment portions 261, 261' until a retrieval force threshold has been exceeded. This arrangement prevents the struts 231, 231' from being inadvertently released or removed from the expandable member 251, 251'. Although the blood pump assembly 200 is shown as including two struts within each set of struts, in other embodiments, the blood pump assembly 200 (and any of the blood pump assemblies described herein) can include any suitable number of struts (e.g., between two and eight, between two and ten, or between two and 12).

Figure 8:
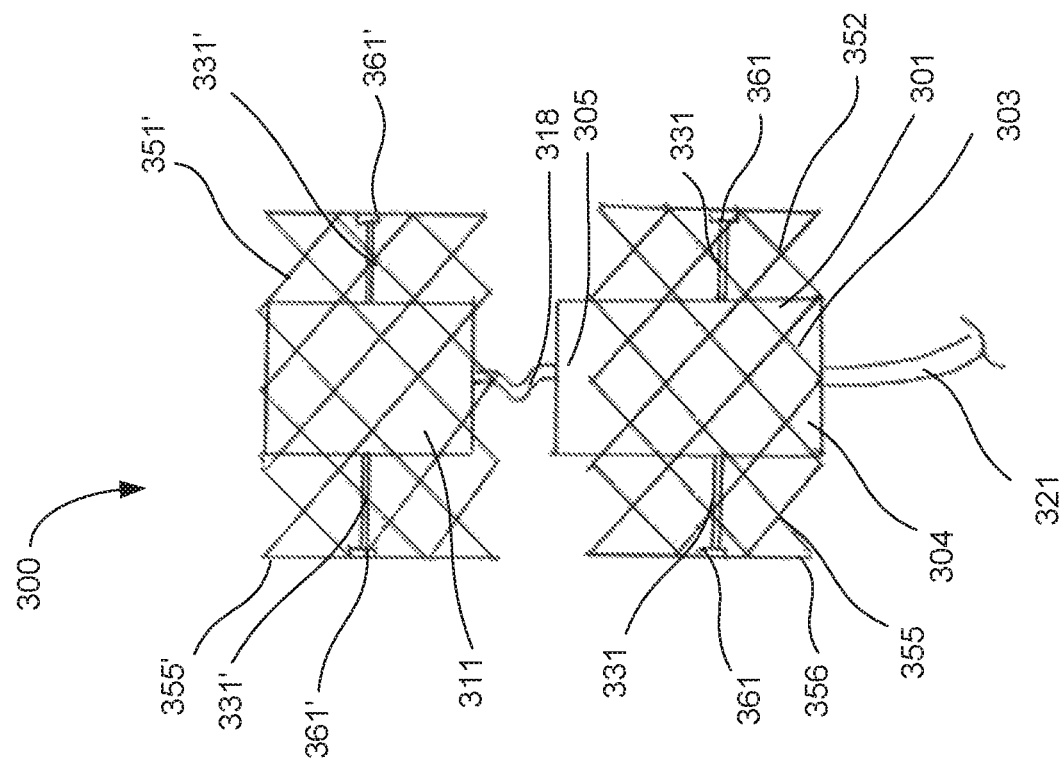
FIG. 8 is a schematic illustration of a blood pump assembly, according to an embodiment.

Although the housing 203 is described as including, in some embodiments, a close-coupled power supply, in other embodiments, a blood pump assembly can include a blood pump and a separately attached, but closely coupled power supply. In this manner, the power supply can be coupled along with the blood pump within the vasculature. This arrangement eliminates the need for passages, tubes, and/or wires to be extended outside of the body, and therefore this arrangement facilitates the long-term use of the pump assembly. Specifically, in some embodiments, a blood pump assembly includes a blood pump and power supply that are coupled by a flexible electrical lead that allows the pump and power supply to articulate relative to each other. In this manner, the assembly can be more easily advanced through tortuous passageways of the vasculature (e.g., the aortic arch). For example, FIG. 8 is a schematic illustration of a blood pump assembly 300, according to an embodiment. Like the blood pump assemblies 100 and 400, the blood pump assembly 200 can be transitioned between a first configuration (collapsed), a second configuration (expanded deployed) and a third configuration (pump retrieved). The blood pump assembly 300 includes a blood pump 301, a power supply 311, two sets of struts 331, 331', and two expandable members 351, 351'. The blood pump 301 can be any suitable device that pumps blood and provides the desired flow characteristics to supplement the output of the heart. For example, the blood pump 301 (and any of the blood pumps described herein) includes a pumping unit (not shown, e.g., an impeller, a roller, a balloon, or the like) enclosed within a housing 303. An inflow cannula 321 is coupled to the distal end portion 304 of the housing 303. The blood pump 301 produces any suitable blood flow rate, for example a flow rate of between 0.5 liters per minute and 3 liters per minute. In some embodiments, the blood pump 301 (or any of the blood pumps described herein) can produce a flow rate of between 1.0 liters per minute and 2.5 liters per minute. Moreover, the blood pump 301 (and any of the blood pumps described herein) can be configured to limit the amount of heat transfer into the blood, reduce and/or eliminate points of stasis, or the like.

As shown, the assembly 300 includes a power supply 311 that is coupled to the blood pump 301 by the electrical lead 318. Specifically, the electrical lead 318 is coupled to the proximal end portion 305 of the housing 303 such that the blood pump 301 and the power supply 301 are axially aligned. Moreover, the electrical lead 318 is flexible such that the pump 301 and the power supply 311 can articulate relative to each other. In this manner, the assembly 300 can be more easily advanced through tortuous passageways of the vasculature (e.g., the aortic arch). The electrical lead 318 can have any suitable length such that the power supply 311 is closely-coupled to the blood pump 301, while still maintaining the desired flexibility for implantation. For example, in some embodiments, the length of the electrical lead 318 is less than the length of the blood pump 301. Specifically, in some embodiments, the length of the electrical lead 318 can be between about 0.25 and 0.75 of the length of the blood pump 301. By maintaining a relatively short distance between the blood pump 301 and the power supply 311, the assembly 300 can be implanted in the ascending aorta without the power supply obstructing the brachiocephalic artery, the left common carotid artery, or the left subclavian artery. In other embodiments, however, the length of the electrical lead 318 can be less than the length of the blood pump 301.

The power supply 311 can include any suitable components of the types shown and described herein to provide power to the blood pump 301 within the vasculature. For example, the power supply 311 includes an energy storage member (not shown), such as a battery, a capacitance storage system, or the like. In some embodiments, the power supply 311 can also include a charging module that can be electromagnetically coupled to an external power supply (not shown). In this manner, the energy storage member (and the power supply 311) can be recharged wirelessly, allowing for long term installation of the system. The charging module can include, for example, a receiving coil (not shown) configured to be electromagnetically coupled to an external power transmission coil (not shown). The charging module can be similar to any of the charging modules or systems shown and described herein (e.g., the wireless systems 781, 800).

The first expandable member 351 is coupled to the housing 303, and is configured to transition from a collapsed configuration to an expanded configuration. The first expandable member 351 includes a series of flexible segments 352 coupled together in any suitable pattern to form a tubular wall 355 having an outer surface 356 and an inner surface, and that defines an interior volume. The second expandable member 351' is coupled to the power supply 311, and is configured to transition from a collapsed configuration to an expanded configuration. Like the first expandable member 351, the second expandable member 351' includes a series of flexible segments coupled together in any suitable pattern to form a tubular wall 355' having an outer surface and an inner surface, and that defines an interior volume.

The expandable members 351, 351' can include any suitable number of flexible segments (e.g., the flexible segments 352) in any suitable form, such as coiled members, longitudinal members, or the like. For example, in some embodiments, the flexible segments can be braided or woven to produce the tubular wall that can transition from the collapsed configuration to the expanded configuration. In some embodiments, the expandable member can include multiple layers of flexible segments to produce the desired spring characteristics and strength. In yet other embodiments, the flexible segments can be produced from a monolithic sheet of material (e.g., by a laser cutting process). Moreover, any the tubular walls 355, 355' (and any of the tubular walls described herein) can have any suitable pore size (or arrangement of openings) so that the outer surface provides the desired contact area within the bodily lumen, as described herein. In this manner, as described herein, the expandable members 351, 351' can be resistant to migration and can provide support for the blood pump 301 and the power supply 311.

When in the expanded configuration, first expandable member 351 is spaced apart from the second expandable member 351'. In this manner, the overall length of contact between the outer surfaces of the expandable members is greater than the sum of the contact length of each of the expandable members. As shown, the overall contact length (i.e., the length along the axial centerline CL from the distal-most portion of the first expandable member 351 to the proximal-most portion of the second expandable member 351') is about the same as the length of the pump 301 and the power supply 311. In other embodiments, however, a ratio between the overall contact length and the length of the collective length of the blood pump 301 and the power supply 311 can be at least about 1.2, 1.4, 1.6, 1.8 or 3.0. The overall length can be limited by, for example, the flexibility to advance the blood pump assembly 300 within the vasculature of the patient (e.g., through the aortic arch) using endovascular techniques, as described herein. In other embodiments, the overall contact length can be less than the collective length of the blood pump 301 and the power supply 311. For example, in some embodiments, a ratio between the overall contact length and the collective length of the blood pump 301 and the power supply 311 can be at least about 0.6, 0.8, or 0.9.

When the blood pump assembly 300 is deployed within a blood vessel (not shown) and the expandable members 351, 351' are in their expanded configurations, the outer surfaces of the tubular walls 355, 355' can contact the inner surface of the blood vessel to maintain (or anchor) the expandable members 351, 351' within the blood vessel. By providing the anchoring force circumferentially and along the axial length of each expandable member 351, 351', as well as the overall contact length, the blood pump assembly 300 is resistant to migration (i.e., movement along the longitudinal center line of the assembly) within the blood vessel. Similarly stated, the expandable members 351, 351' distribute the radially outward anchoring force over the contact area of the outer surfaces of each expandable member, thereby minimizing migration. This arrangement also minimizes and/or eliminates tipping (i.e., rotation about an axis non-parallel to the longitudinal center line CL). Moreover, by avoiding anchoring via discrete anchor points, the expandable member 351 and the blood pump assembly 300 reduces the likelihood of perforating the wall of the blood vessel.

The first expandable member 351 and the second expandable member 351' each include a series of attachment portions 361, 361' to which a corresponding strut 331, 331' can be removably and/or releasably coupled. In some embodiments, the attachment portions 361, 361' (and any of the attachment portions described herein) can be a separate structure or mechanism that is coupled to the flexible segments or tubular wall 355, 355' of each expandable member. In other embodiments, the attachment portions 361, 361' (and any of the attachment portions described herein) can be monolithically constructed with (or a portion of) their respective flexible segments or tubular wall. Although the expandable members 351, 351' are shown as including two attachment portions 361, 361', in other embodiments, the expandable members 351, 351' (and any of the expandable members described herein) can include any suitable number of attachment portions (e.g., between two and eight, between two and ten, or between two and 12). Although the attachment portions 361, 361' are shown as extending within the internal volume, in other embodiments, the attachment portions 361, 361' can be flush with the inner surface of the tubular walls 355, 355'. Similarly stated, in some embodiments, the tubular walls 355, 355' and the respective set of attachment portions 361, 361' define a continuous inner surface.

The blood pump assembly 300 includes two sets of struts 331, 331'. The first set of struts 331 correspond to the first expandable member 351 and the second set of struts 331' correspond to the second expandable member 351'. Each strut 331, 331' includes a first end portion and a second end portion. The first end portion of each strut 331, 331' is coupled to the pump 301 and/or the housing 303. The first end portion can be coupled to the housing 303 in any suitable manner, such as a pin joint or a ball joint. In this manner, the struts 331, 331' can rotate or otherwise move relative to the housing (e.g., when the expandable members 351, 351' move from their collapsed configuration to their expanded configuration). In other embodiments, the first end portion of each strut can be coupled to the housing 303 by a band, weld joint, or adhesive. The struts 331, 331' can be coupled to the housing 303 at any suitable strut angle θ with the axial centerline of the housing 303 or the power supply 311.

The second end portion of each strut 331, 331' is removably coupled to its corresponding attachment portion 361, 361'. In this manner, the blood pump 301 and the power supply 311 can be removably coupled to the expandable members 351, 351' by the two sets of struts 331 331'. Similarly stated, when the blood pump assembly 300 is in its first configuration and its second configuration, the blood pump 301 and the power supply 311 are suspended within the interior volume of the expandable members 351, 351' by the two sets of struts 331, 331'. Because the second end portion of each strut is removably (or releasably) coupled to the corresponding attachment portion, the blood pump 301, the power supply 311, and the struts 331, 331' can be removed from the expandable members 351, 351' by any of the methods described herein.

In some embodiments, either of the attachment portions 361, 361' or the struts 331, 331' can include a latch, a locking mechanism, or detent that maintains the struts 331, 331' within the attachment portions 361, 361' until a retrieval force threshold has been exceeded. This arrangement prevents the struts 331, 331' from being inadvertently released or removed from the expandable member 351, 351'. Although the blood pump assembly 300 is shown as including two struts within each set of struts, in other embodiments, the blood pump assembly 300 (and any of the blood pump assemblies described herein) can include any suitable number of struts (e.g., between two and eight, between two and ten, or between two and 12).

Figure 10:
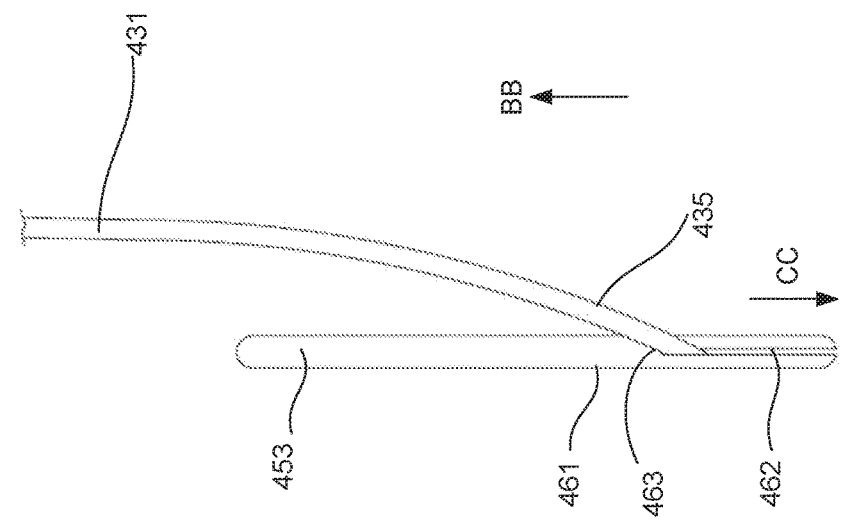
FIG. 10 is an enlarged view of a portion of the blood pump assembly shown in FIG. 9.
Figure 9:
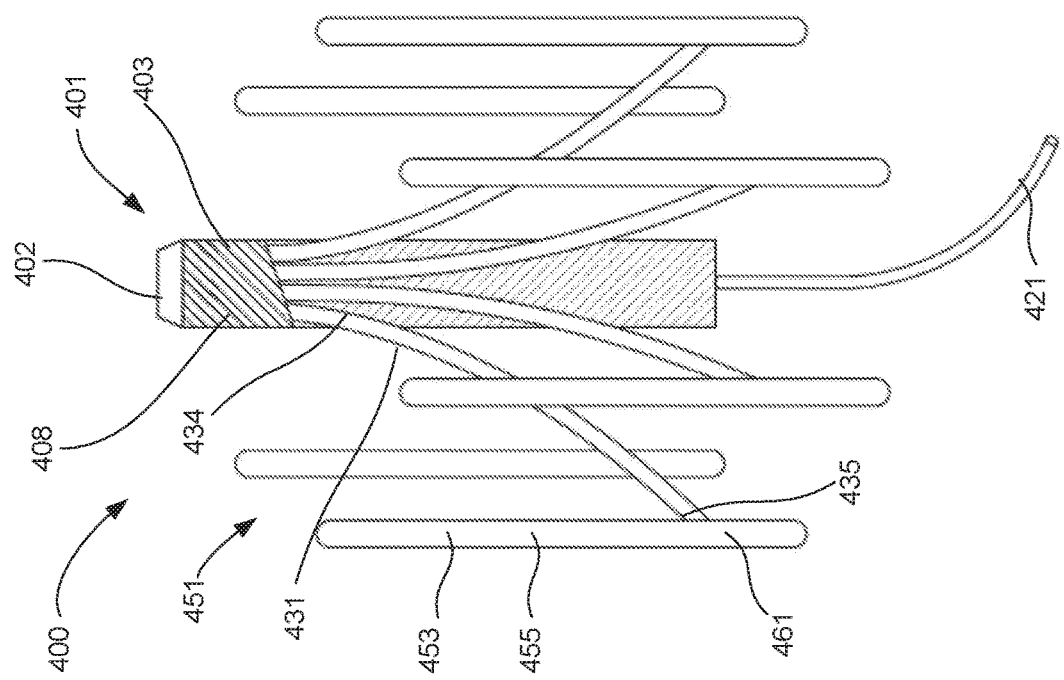
FIG. 9 is front perspective view of a blood pump assembly, according to an embodiment.
Figure 11:
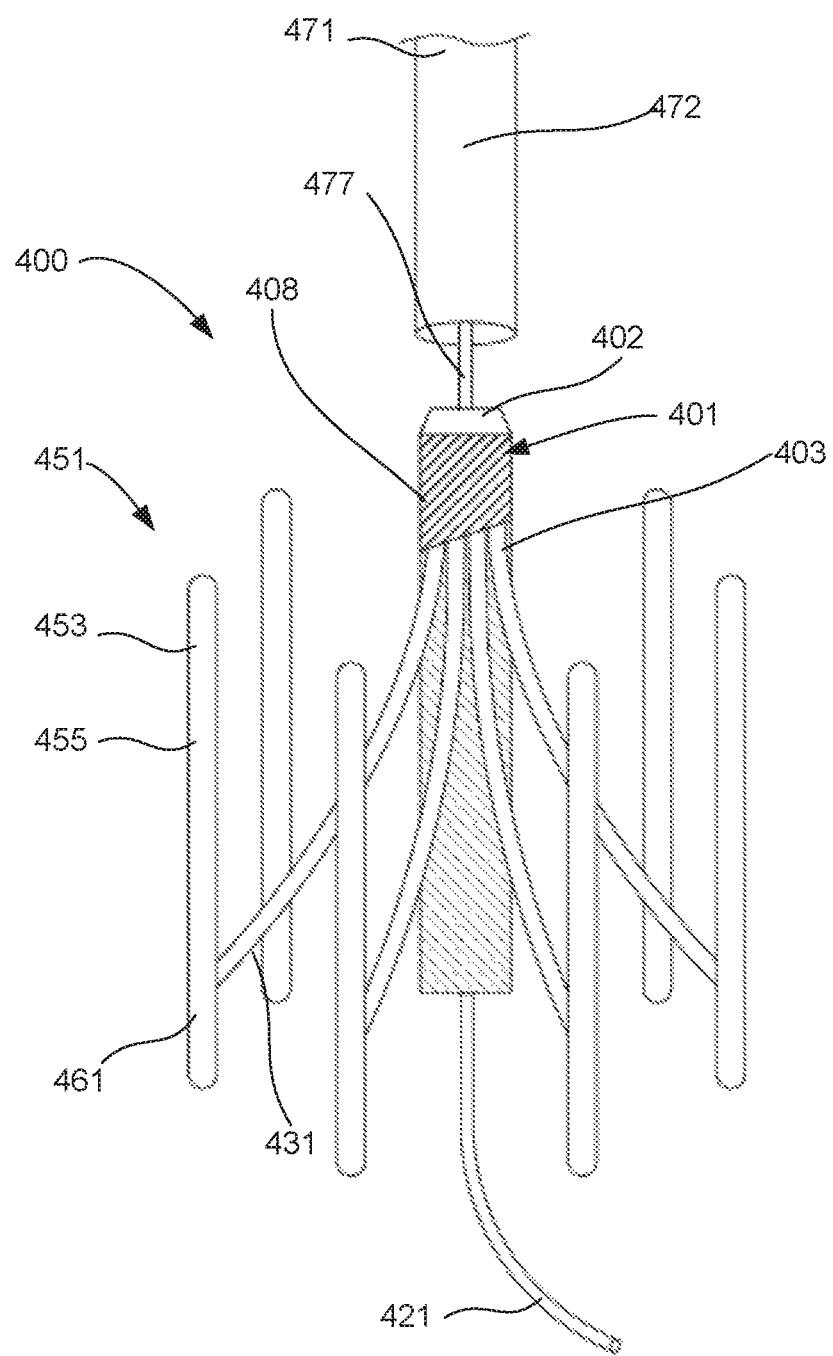
FIGS. 11-13 show the blood pump assembly shown in FIG. 9 in various stages of being transitioned from its second (or deployed) configuration and its third (or removed) configuration.
Figure 13:
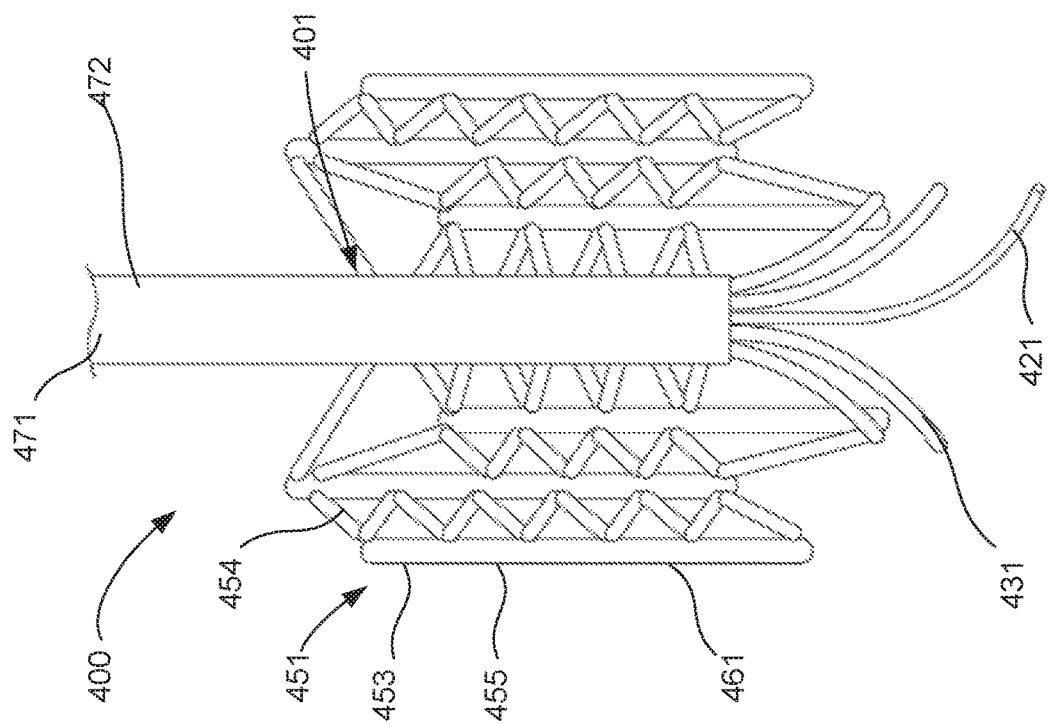
Figure 12:
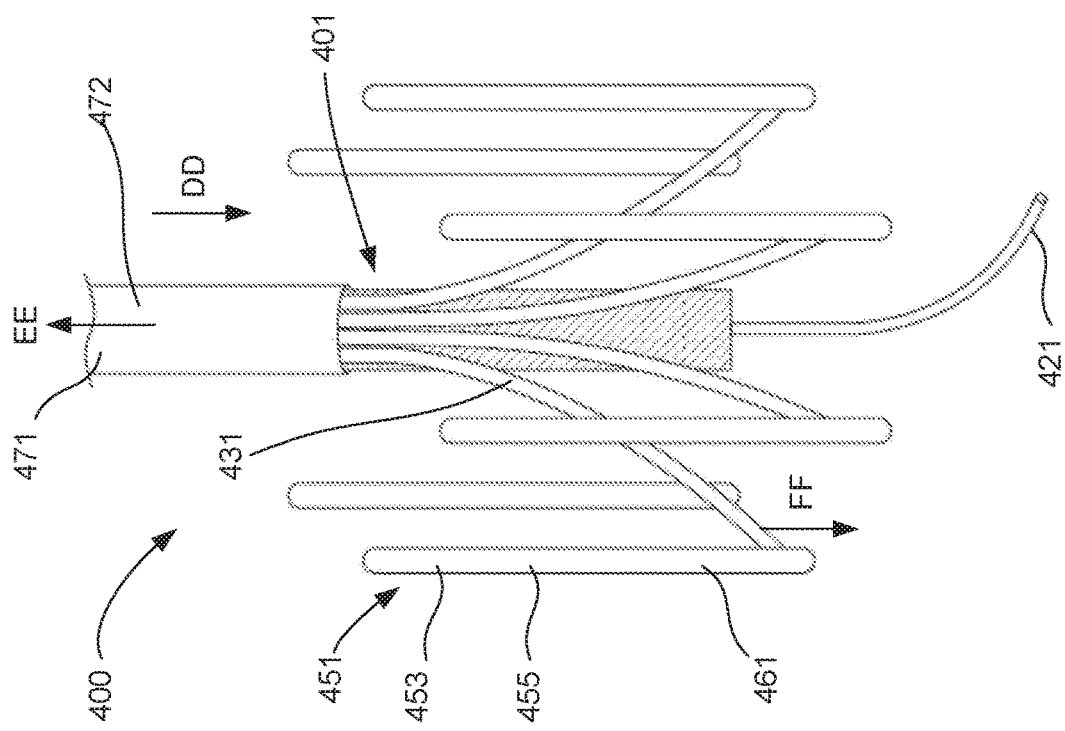

FIGS. 9-13 are show a blood pump assembly 400, according to an embodiment, that can be transitioned between a first configuration (collapsed), a second configuration (expanded and deployed) and a third configuration (pump retrieved). The blood pump assembly 400 is shown in the second configuration (FIGS. 9 and 10), and in various stages of being transitioned to the third configuration (FIGS. 11-13). The blood pump assembly 400 includes a blood pump 401, a set of struts 431 (only one strut is labeled), and an expandable member 451. The blood pump 401 can be any suitable device that pumps blood and provides the desired flow characteristics to supplement the output of the heart. For example, the blood pump 401 (and any of the blood pumps described herein) includes a pumping unit (not shown, e.g., an impeller, a roller, a balloon, or the like) enclosed within a housing 403. The blood pump 401 produces any suitable blood flow rate, for example a flow rate of between 0.5 liters per minute and 3 liters per minute. In some embodiments, the blood pump 401 (or any of the blood pumps described herein) can produce a flow rate of between 1.0 liters per minute and 2.5 liters per minute. In some embodiments, the assembly 400 can include a power supply (not shown) that is close-coupled to the blood pump 401, either within the housing 403 or within a separate housing (e.g., similar to the power supply 311 described above). Similarly stated, in some embodiments the assembly 400 (or any of the assemblies described herein) can include a power supply (battery, capacitance power supply, etc.) that can be disposed along with the blood pump 401 within the vasculature. In such embodiments, the assembly 400 (or any of the assemblies described herein) can also include a wireless charging system of the types shown and described herein (e.g., the wireless systems 781, 800).

The proximal end of housing 403 includes a proximal attachment portion 402 and an attachment band 408. The proximal attachment portion 402 is used for retrieval of the pump, as described herein, and can include any mechanism for attaching the retrieval wire 477 to the pump 401 (see FIG. 11). For example, in some embodiments, the proximal attachment portion 402 can include a hook, a threaded portion, a magnetic coupling mechanism, or the like. The distal end portion of the housing 403 is coupled to an inflow cannula 421.

The expandable member 451 is configured to transition from a collapsed configuration (not shown) to an expanded configuration (FIGS. 9-13), and includes a series of flexible segments. The flexible segments include both longitudinal segments 453 and lateral segments 454 (see FIG. 13), which can be coupled together in any suitable pattern to form a tubular wall 455. The tubular wall 455 has an outer surface and an inner surface, and defines an interior volume, similar to that formed by the expandable members 151, 251, 351 described herein. The expandable member 451 can include any suitable number of flexible segments in any suitable form, such as coiled members, longitudinal members, or the like. For example, in some embodiments, the flexible segments (e.g., the lateral segments 454) can be braided or woven to produce the tubular wall 455 that can transition from the collapsed configuration to the expanded configuration. In some embodiments, the expandable member 451 can include multiple layers of flexible segments to produce the desired spring characteristics and strength. In yet other embodiments, the flexible segments can be produced from a monolithic sheet of material (e.g., by a laser cutting process). Moreover, any the tubular wall 455 (and any of the tubular walls described herein) can have any suitable pore size (or arrangement of openings) so that the outer surface provides the desired contact area within the bodily lumen. In this manner, the expandable member can be resistant to migration and can provide support for the blood pump 401 suspended within the interior volume.

When the blood pump assembly 400 is deployed within a blood vessel (not shown) and the expandable member 451 is in its expanded configuration, the outer surface of the tubular wall 455 is in contact with an inner surface of the blood vessel. The expandable member 451 is sized and configured such that the outer surface exerts a radially outward force on the inner surface to maintain (or anchor) the expandable member 451 within the blood vessel. By providing the anchoring force circumferentially and along the axial length of the expandable member 451 (as opposed to multiple, discrete anchor points), the expandable member 451 and the blood pump assembly 400 are resistant to migration (i.e., movement along the longitudinal center line) within the blood vessel. This arrangement also minimizes and/or eliminates tipping (i.e., rotation about an axis non-parallel to the longitudinal center line). Moreover, by avoiding anchoring via discrete anchor points, the expandable member 451 and the blood pump assembly 400 reduces the likelihood of perforating the wall of the blood vessel.

The expandable member 451 includes a series of attachment portions 461 (only one is labeled) to which a corresponding strut 431 can be removably and/or releasably coupled. Although the attachment portions 461 are shown as being monolithically constructed along with the longitudinal segments 453, in other embodiments, the attachment portions 461 (and any of the attachment portions described herein) can be a separate structure or mechanism that is coupled to the longitudinal segments 453 or tubular wall 455. Moreover, because the attachment portions 461 are monolithically constructed as a part of the longitudinal segments 453, the attachment portions 461 do not extend into or otherwise obstruct the interior volume of the expandable member. Similarly stated, the attachment portions 461 can be flush with (or form a continuous surface with) the inner surface 458 of the tubular wall 455. In this manner, when the blood pump 401 is removed and the expandable member 451 is left within the body, the blood vessel will remain unobstructed. This arrangement also facilitates the implantation of a second blood pump assembly at the same location as (or on top of) the remaining expandable member. Although the expandable member 451 is shown as including six attachment portions 461, in other embodiments, the expandable member 451 (and any of the expandable members described herein) can include any suitable number of attachment portions (e.g., between two and eight, between two and ten, or between two and 12).

Referring to FIG. 10, each attachment portion 461 defines a slot 462 within which the second end portion 435 of the corresponding strut 431 can be slidingly disposed. Moreover, each attachment portion 461 includes a shoulder 463 or "end stop" that resists movement of the second end portion 435 of the corresponding strut 431. In this manner, when the assembly 400 is in the second (deployed) configuration, the second end portion 435 of each strut 431 is disposed within its corresponding slot 462, and is in contact with the shoulder 463. This arrangement prevents movement of the struts 431 in the direction indicated by the arrow BB in FIG. 10. The direction BB is also the direction of blood flow, and thus, the force exerted by the flow of blood produced by the heart acts to maintain the second end portion 435 in contact with the shoulder 463. Thus, when the assembly 400 is in the second (deployed) configuration, the second end portion 435 of each strut 431 is firmly and stably attached to the corresponding attachment portion 461.

As described in more detail below, to remove the blood pump 401 and the struts 431, a distal force (as indicated by the arrow CC) is applied to the struts 431. When the distal retrieval force exceeds a threshold value, the second end portion 435 of the corresponding strut 431 can slide distally within the slot 462 to a position outside (and released from) the attachment portion 461. In some embodiments, either of the attachment portions 461 or the second end portion 435 of the struts 431 can include a latch, a locking mechanism, or detent that maintains the struts 431 within their respective slots 462 until the retrieval force threshold has been exceeded. This arrangement prevents the struts 431 from being inadvertently released or removed from the expandable member 451.

The blood pump assembly 400 includes a set of struts 431. Each strut 431 includes a first end portion 434 and a second end portion 435. The first end portion 434 of each strut 431 is coupled to the housing 403 by the attachment band 408. In other embodiments, however, the first end portion 434 can be coupled by a pin joint or a ball joint, such that the strut 431 can rotate relative to the housing (e.g., when the expandable member 451 moves from its collapsed configuration to its expanded configuration). In other embodiments, the first end portion 434 can be coupled to the housing 403 by weld joint or adhesive.

As described above, the second end portion 435 of each strut is removably coupled within the slot 462 of its corresponding attachment portion 461 of the expandable member 451. In this manner, the blood pump 401 can be removably coupled to the expandable member 451 by the set of struts 431. More particularly, the blood pump 401 can be coupled to the expandable member 451 with at least a portion of the housing 403 disposed within the interior volume (not identified) of the expandable member 451. In some embodiments, the second end portion 435 can include a hook, latch, or the like that engages the shoulder 463. Similarly stated, in some embodiments, the second end portion 435 includes a protrusion having a longitudinal centerline that is offset from a centerline of the strut 431 (i.e., a curved or hooked portion). In some embodiments, the second end portion 435 of the struts 431 can include a latch, a locking mechanism, or detent that maintains the struts 431 within the slot 462 until a retrieval force threshold has been exceeded.

Because the second end portion 435 of each strut is removably (or releasably) coupled to the corresponding attachment portion 461, the blood pump 401 and the struts 431 can be removed from the expandable member 451. This arrangement allows the blood pump assembly 400 to be moved from the second configuration (FIGS. 9 and 10) to the third configuration (FIG. 13). In this manner, the blood pump 401 and the struts 431 can be removed when the assembly 400 is within the body, for example, if the patient no longer needs the pump assembly 400, if the blood pump 401 has malfunctioned, or the like. Moreover, the blood pump 401 and the struts 431 can be removed endoscopically by decoupling (or releasing) the struts 431 from the attachment portions 461.

Although the blood pump assembly 400 is shown as including four struts 431, in other embodiments, the blood pump assembly 400 (and any of the blood pump assemblies described herein) can include any suitable number of struts (e.g., between two and eight, between two and ten, or between two and 12).

In use, the blood pump assembly 400 (and any of the blood pump assemblies described herein) can be implanted into a patient's circulatory system to supplement the blood flow output of the heart. Any suitable endovascular, minimally-invasive and/or percutaneous techniques can be used to implant the blood pump assembly 400, according to any of the methods described herein. Moreover, because the blood pump 401 and the struts 431 can be removed from the expandable member 451, the blood pump assembly 400 (and any of the blood pump assemblies described herein) is well suited for both short term and long term use. For example, the blood pump assembly 400 (and any of the blood pump assemblies described herein) can be implanted, and then removed within ten days, one month, two months, or less than one year when the patient no longer needs the circulatory assistance. As described herein, the blood pump 401 and the struts 431 can be removed (leaving the expandable member 451 behind) without obstructing the blood vessel. Similarly, when implanted for long-term use (e.g., one year, two years, or longer), the blood pump 401 and the struts 431 can be removed when there is a failure of the blood pump 401, to replace the batteries (not shown) or the like.

To implant the blood pump assembly 400, the assembly 400 is first inserted into an entry blood vessel (e.g., the femoral artery) endovascularly. Similarly stated, the assembly 400 is first inserted into an entry blood vessel (e.g., the femoral artery) using percutaneous and/or minimally invasive techniques. The blood pump assembly 400 is inserted when in its first (or collapsed) configuration. The blood pump assembly 400 is then advanced to a target blood vessel (not shown). The target blood vessel can be any suitable blood vessel, such as the descending aorta, the aortic arch, or the ascending aorta. The blood pump assembly 400 is then transitioned from its first (or collapsed) configuration to its second (or expanded configuration). When in the expanded configuration, the outer surface of the tubular wall 455 contacts, engages and/or exerts a radially outward force upon the inner surface of the blood vessel to anchor the blood pump assembly 400 within the blood vessel.

After being implanted, the blood pump 401 can be actuated (or powered) to supplement the blood flow provided by the patient's heart. In particular, the blood pump 401 (and any of the blood pumps described herein) can supplement the blood flow continuously or only during diastole. As shown in FIG. 4, the blood pump 401 can receive an inlet blood flow via the inlet cannula 421 and produce an outlet blood flow. Because the blood pump 401 is suspended with the blood vessel, the blood flow produced by the heart (e.g., during systole) can flow around the blood pump 401.

When removal of the blood pump 401 is desired, the struts 431 can be detached from attachment portions 461 of the expandable member 451, and the blood pump 401 and the struts 431 can be removed. Referring to FIG. 11, a retrieval tool 471 is advanced to the target blood vessel using endovascular techniques as described herein. The retrieval tool 471 includes a retrieval wire 477 and a retrieval sheath 472. The retrieval wire is coupled to the proximal attachment portion 402. As shown by the arrow EE in FIG. 12, a proximal force can be exerted on the pump housing 403 to maintain the pump 401 within the blood vessel at a desired and/or constant position. The retrieval sheath 472 is advanced distally as shown by the arrow DD. An edge of the retrieval sheath 472 contacts the struts 431 as the sheath moves distally, thereby exerting a distal force upon the struts 431. When the distal force is sufficient to overcome the retrieval force threshold (e.g., the resistance of the blood flow, the resistance of the detent, etc.), each of the struts 431 moves distally within the slots 462, as shown by the arrow FF in FIG. 12. Continued movement of the sheath 472 releases the struts 431 from their respective attachment portions 461, and allows the blood pump 461 and the struts 431 to be enclosed within the sheath 472 for withdrawal from the body.

Removal in this manner leaves only the expandable member 451 with the blood vessel, which does not block the blood vessel. The design of the expandable member 451 can facilitate installation of a second (e.g., a replacement) pump assembly directly on top of the existing expandable member. Moreover, by removing the struts 431 from the expandable member 451, as opposed to removing the end portion of the struts 431 directly from the inner surface of the blood vessel, the risk of perforation or tearing of the blood vessel is minimized Specifically, because implanted structure that is in direct contact with the inner surface may be subject to tissue ingrowth, endothelialization, or the like, the arrangement of the assembly 400 provides a reliable way to remove the blood pump 401 via endovascular techniques and with minimal risk of damaging the blood vessel.

Figure 14:
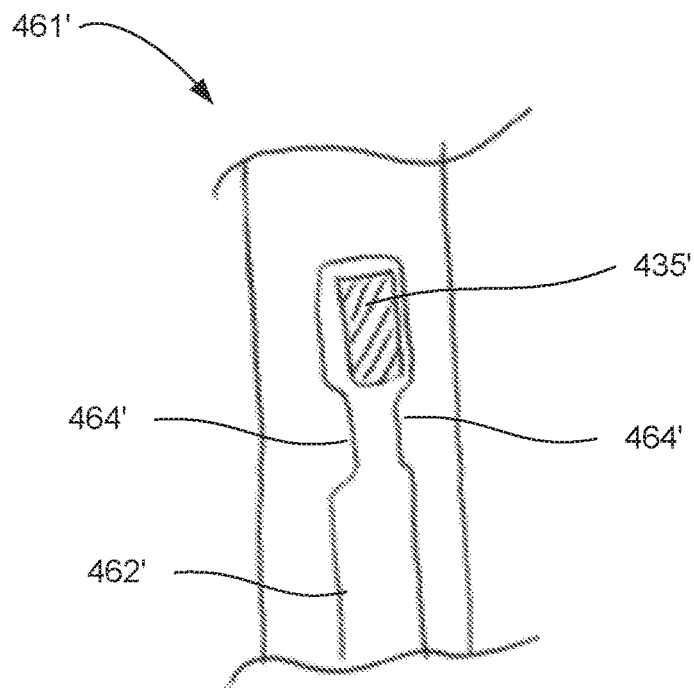
FIGS. 14 and 15 are schematic illustrations of attachment portions according to various embodiments.

Although the attachment portions 461 are shown and described above as defining the slots 462 within which the second end portion 435 of the respective strut 431 is disposed, in other embodiments, the struts can define the slots within which a protrusion of the attachment portions are slidingly disposed. Moreover, any suitable detent or resistance mechanism can be included. For example, FIG. 14 shows an attachment portion 461' that defines a slot 462' within which a strut 435' can be disposed. The attachment portion 461' includes protrusions 464' that resist the distal movement of the strut 435' until a retrieval force threshold has been exceed.

Figure 15:
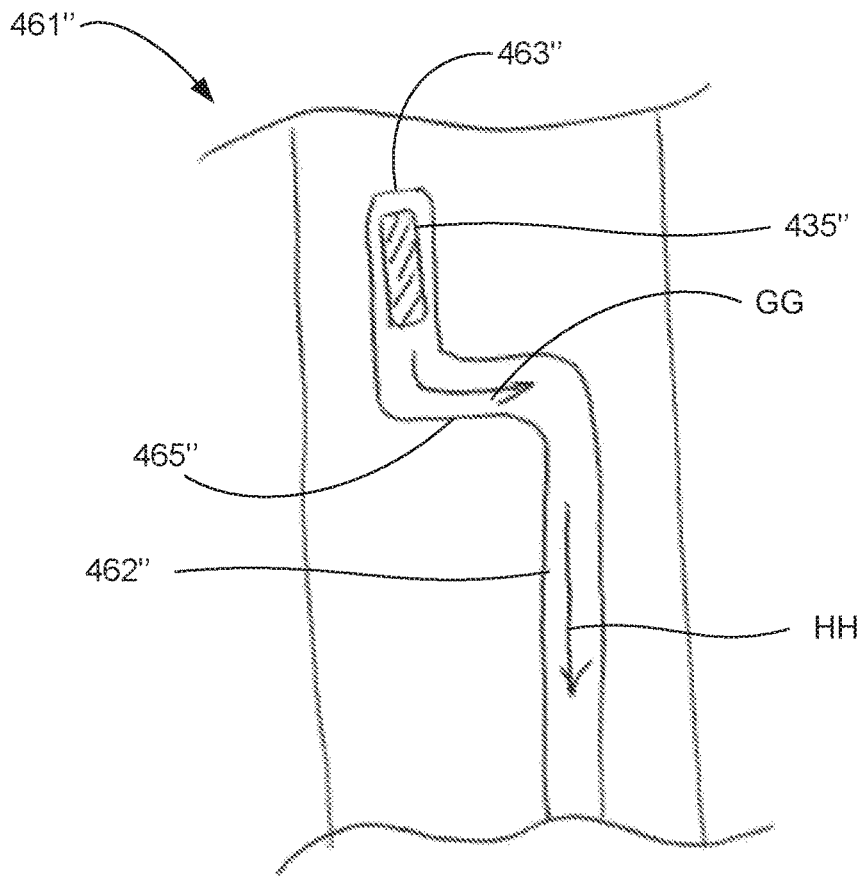

FIG. 15 shows an attachment portion configured to enable a "twist-lock" type retrieval mechanism. In particular, FIG. 15 shows an attachment portion 461" that defines a slot 462" within which a strut 435" can be disposed. The slot 462" is bounded by a proximal shoulder 463" that prevents proximal movement of the strut 435" and a twist-lock shoulder 465" that limits (but does not prevent) distal movement of the strut 435" during retrieval. To remove the strut 435" the strut 435" must be rotated as indicated by the arrow GG before it can be moved distally within the slot (arrow HH).

Figure 16:
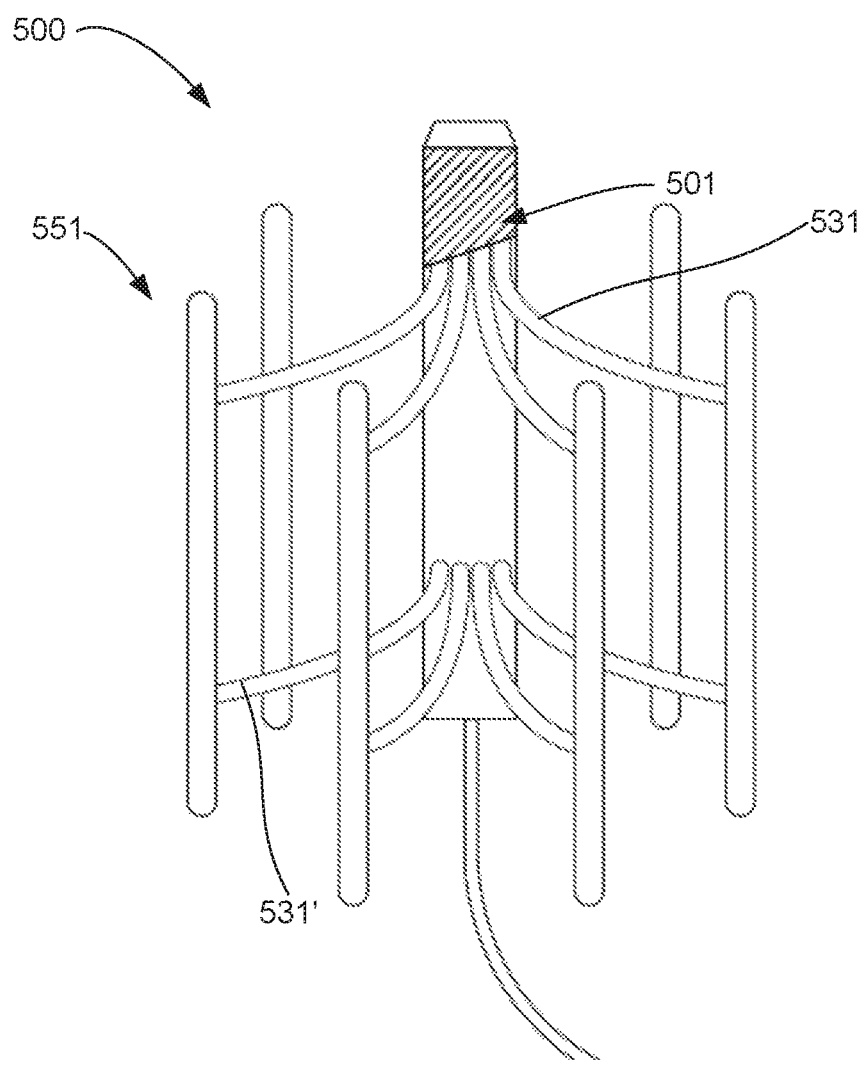
FIG. 16 is front perspective view of a blood pump assembly, according to an embodiment.

Although the blood pump assembly 400 is shown as including one set of struts 431 that is coupled to the proximal end portion of the housing 403, in other embodiments, a blood pump assembly can include any number of struts that are coupled to the pump and/or the power supply in any suitable axial locations. For example, in some embodiments, a blood pump assembly can include multiple sets of struts that couple to the housing, the blood pump and/or the power supply at multiple different axial locations. In this manner, the assembly can reduce the likelihood of tipping and increase the stability of the blood pump within the vasculature. For example, FIG. 16 shows a blood pump assembly 500, according to an embodiment, that can be transitioned between a first configuration (collapsed), a second configuration (expanded and deployed) and a third configuration (pump retrieved). The blood pump assembly 500 includes a blood pump 501, a first set of struts 531 (only one strut is labeled), a second set of struts 531' (only one strut is labeled), and an expandable member 551. The blood pump 501 is similar to the blood pump 401 (and any other blood pump described herein), and is therefore not described in detail. The expandable member 551 is similar to the expandable member 451 in many respects, and is not described in detail. The expandable member 551 differs from the expandable member 451, however, in that the expandable member 551 includes multiple sets of attachment portions (not identified), each corresponding to a strut within the different sets of struts 531, 531'. The attachment portions can be similar to the attachment portions 461 described above. The first set of struts 531 is coupled to the proximal end portion of the blood pump 501, and the second set of struts 531' is coupled to the central portion of the blood pump 501. In this manner, the two sets of struts 531, 531' provide resistance against tipping.

Figure 18:
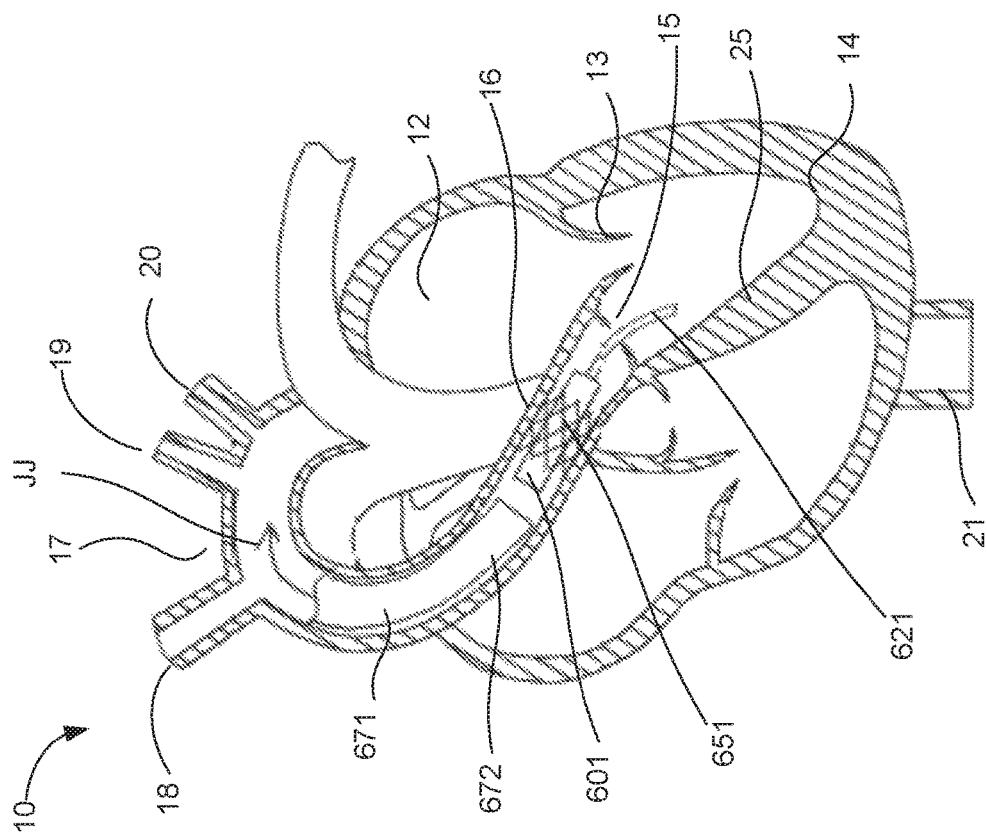
FIGS. 17 and 18 are schematic illustrations showing a method of implanting a blood pump assembly, according to an embodiment.
Figure 17:
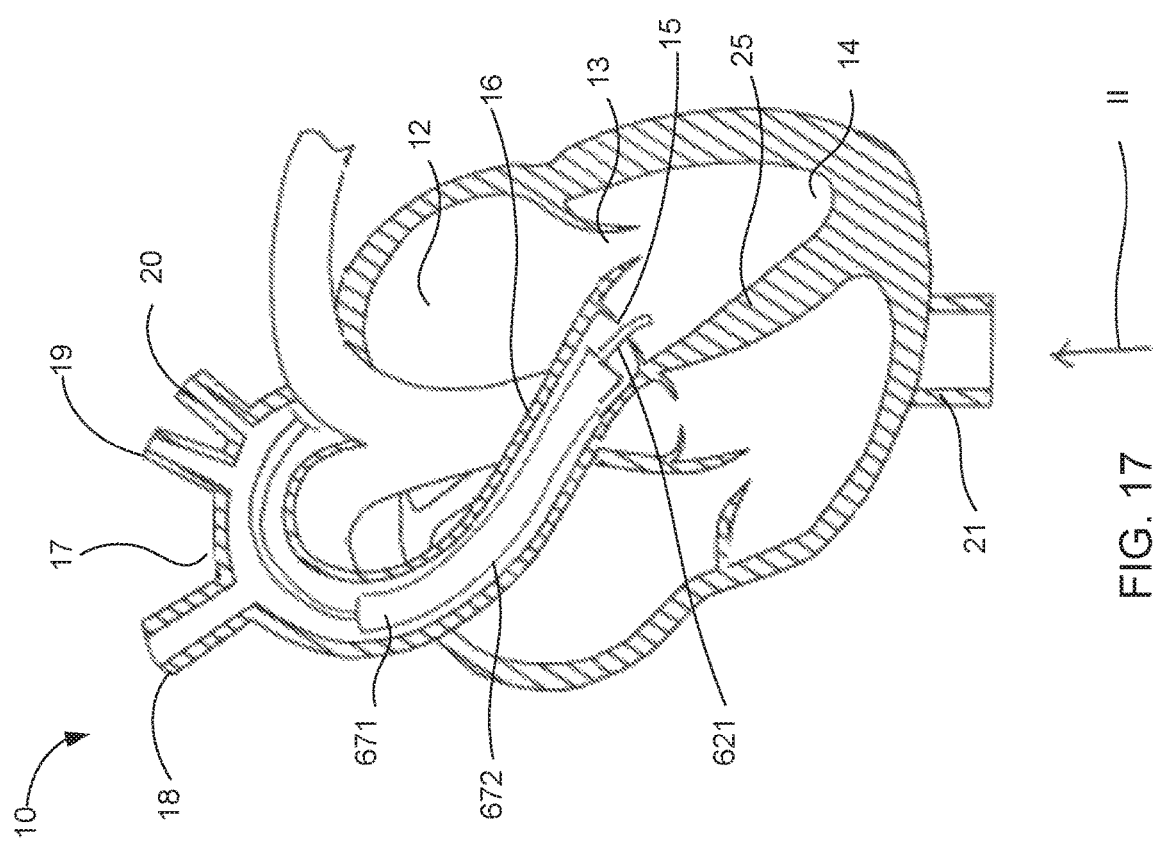
Figure 19:
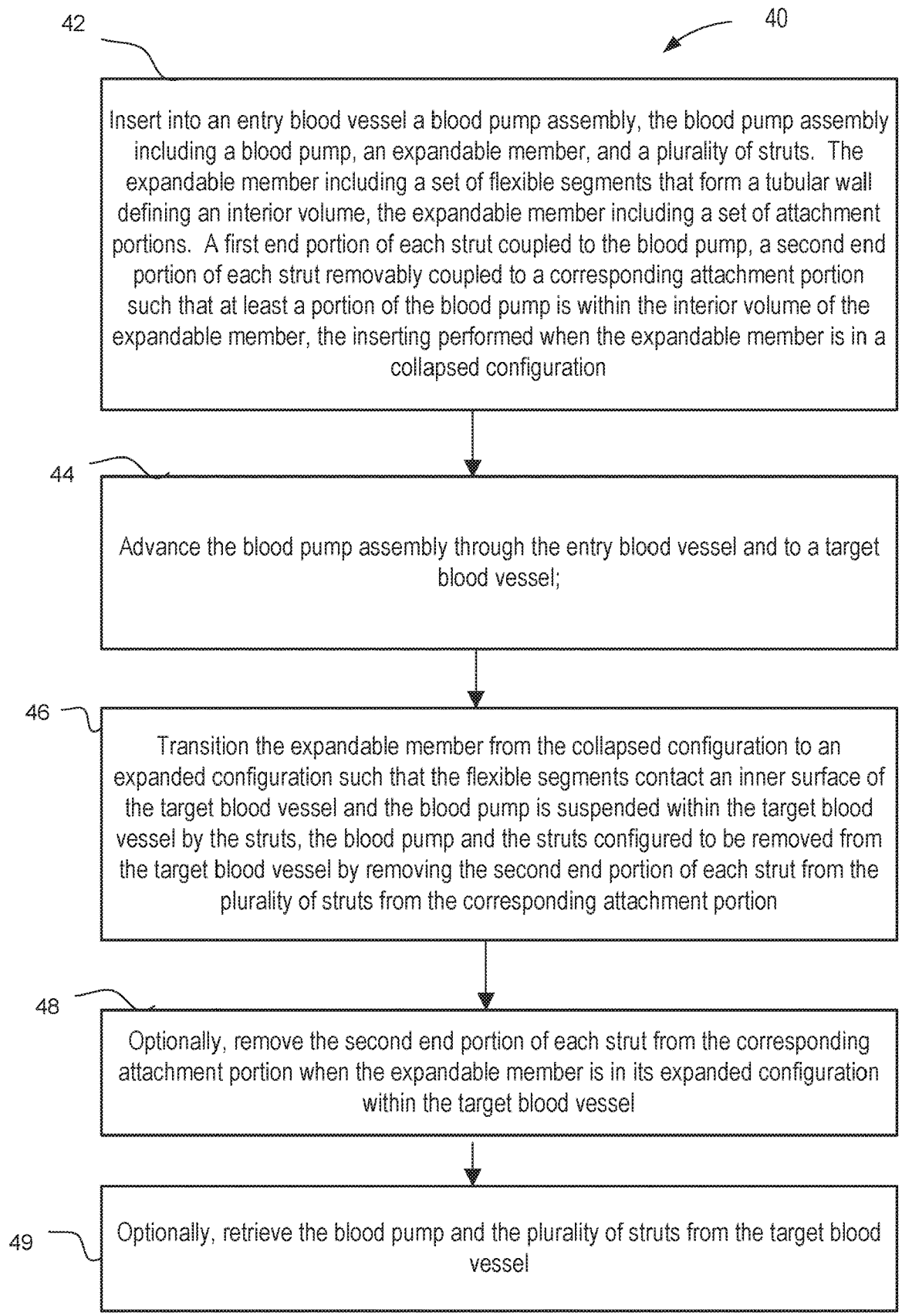
FIG. 19 is a flow chart of a method of implanting a blood pump assembly, according to an embodiment.

In some embodiments, any of the blood pump assemblies shown and described herein can be implanted to any suitable target blood vessel endovascularly. FIG. 19 is a flow chart of a method 40 of implantation of a blood pump assembly, according to an embodiment. The method 40 is also illustrated in FIGS. 17 and 18, which show a schematic illustration of the method of implantation with the heart 10. The method 40 can performed using any of the blood pump assemblies described herein. Although the schematic illustrations in FIGS. 17 and 18 show a blood pump 601 (having an inflow cannula 621) and an expandable member 651, the method can be performed using any of the blood pump assemblies described herein.

The method 40 includes inserting into an entry blood vessel a blood pump assembly, at 42. The blood pump assembly includes a blood pump (see e.g., blood pump 601), an expandable member (see e.g., expandable member 651), and a set of struts (not shown in FIG. 18). The expandable member includes a set of flexible segments that form a tubular wall defining an interior volume, similar to any of the expandable members described herein. The expandable member includes a set of attachment portions. A first end portion of each strut is coupled to the blood pump, and a second end portion of each strut is removably coupled to a corresponding attachment portion such that at least a portion of the blood pump is within the interior volume of the expandable member. As shown in FIG. 17, the inserting performed when the expandable member is in a collapsed configuration.

In some embodiments, the inserting optionally includes percutaneously inserting a catheter (see e.g., the catheter assembly 671 including the sheath 672) that contains the blood pump assembly into the entry blood vessel. In some embodiments, the method includes inserting the blood pump assembly percutaneously into a femoral artery.

Although FIGS. 17 and 18 show the implantation of a blood pump 601, in some embodiments, the method 40 includes inserting a blood pump assembly that includes a power supply coupled to the blood pump and configured to provide power to drive the blood pump. For example, in some embodiments, the method includes inserting a blood pump assembly that includes an integrated power supply (e.g., the assembly 200). In other embodiments, the method includes inserting a blood pump assembly that includes a close-coupled power supply (e.g., the assembly 300).

The blood pump assembly is then advanced through the entry blood vessel and to a target blood vessel, at 44. As shown by the arrow II in FIG. 17, in some embodiments, the catheter assembly 671 can be advanced in a retrograde manner within the descending aorta, through the aortic arch and into the ascending aorta. Thus, in some embodiments, the target blood vessel is the ascending aorta, and the advancing can be performed until the inflow cannula (see cannula 621 in FIGS. 17 and 18) is advanced through the aortic valve and into the left ventricle.

The expandable member is then transitioned from the collapsed configuration to an expanded configuration such that the flexible segments contact an inner surface of the target blood vessel (e.g., the ascending aorta), at 46. In this manner, the blood pump is suspended within the target blood vessel by the struts. The transitioning can be performed by any suitable method. For example, in some embodiments, the sheath 672 can be moved proximally, as shown by the arrow JJ in FIG. 18 to allow the expandable member to be moved outside of the sheath. In some embodiments, the tubular wall of the expandable member is constructed from a shape memory material such that the expandable member assumes its expanded configuration after being removed from the sheath 672. In other embodiments, the catheter assembly 671 can include a balloon that is disposed at least partially within the interior volume of the expandable member. In such embodiments, the balloon can be inflated to exert a radially outward force on the tubular wall to urge the transition from the collapsed configuration to the expanded configuration.

As described herein, the blood pump and the struts are configured to be removed from the target blood vessel by removing the second end portion of each strut from the corresponding attachment portion. Thus, in some embodiments, the method 40 optionally includes removing the second end portion of each strut from the corresponding attachment portion from the plurality of attachment portions when the expandable member is in its expanded configuration within the target blood vessel, at 48. The struts can be removed by any of the methods (or mechanisms) shown and described herein. For example, in some embodiments, the struts can be similar to the struts 431 and can be removed by the methods shown and described above with reference to the blood pump assembly 400. In some embodiments, the method 40 optionally retrieving the blood pump and the plurality of struts from the target blood vessel, at 49.

Figure 20:
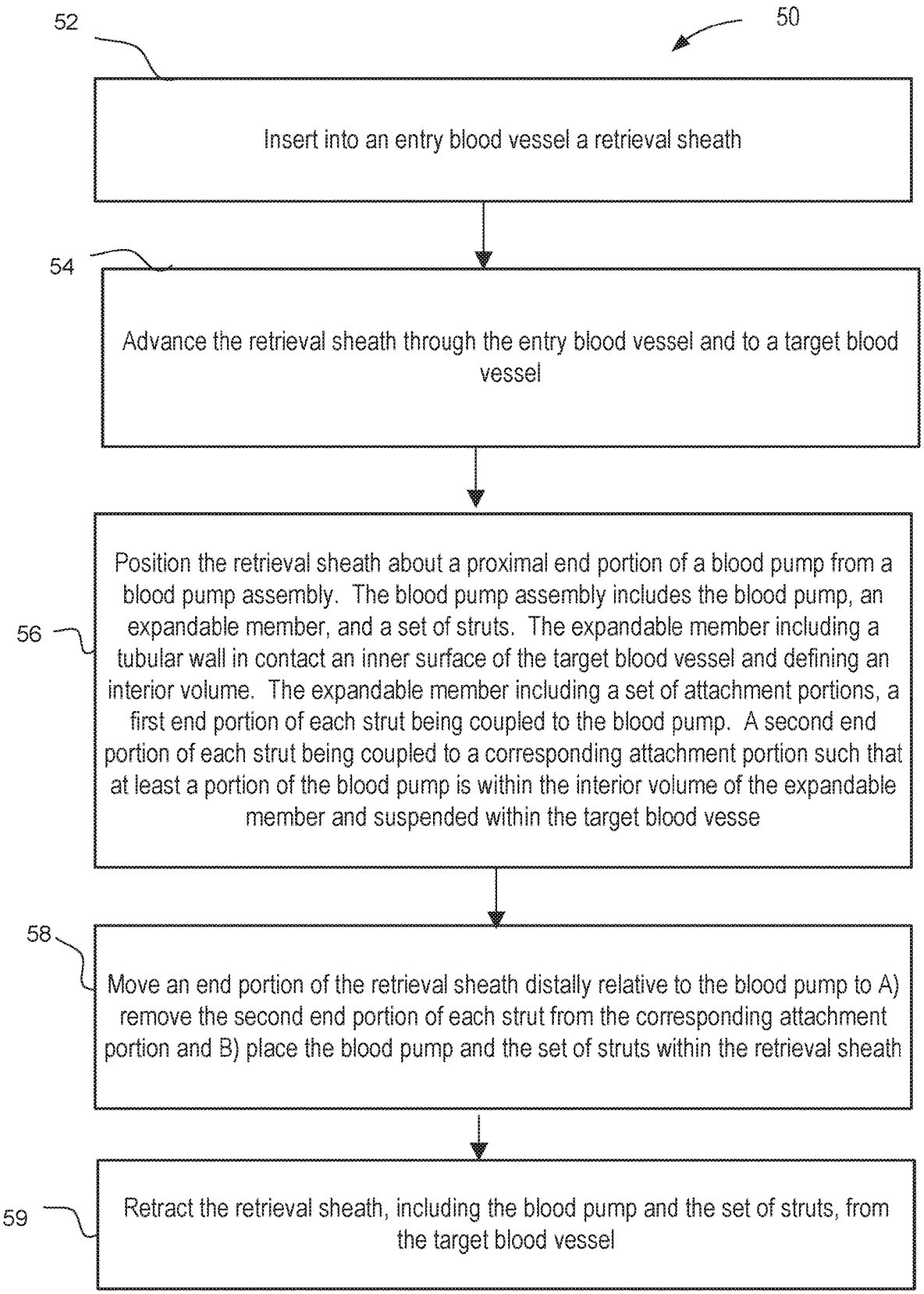
FIG. 20 is a flow chart of a method of retrieving a blood pump assembly, according to an embodiment.

In some embodiments, any of the blood pump assemblies shown and described herein can be retrieved from any of the target blood vessels endovascularly. FIG. 20 is a flow chart of a method 50 of retrieving a blood pump assembly, according to an embodiment. The method 50 can performed using any of the blood pump assemblies described herein. For example, in some embodiments, the method of retrieval can be performed on the blood pump assembly 400 (and using the retrieval tool 471) shown and described in FIGS. 9-13.

The method 50 includes inserting into an entry blood vessel a retrieval sheath, at 52. The entry blood vessel can be, for example, a femoral artery. In other embodiments, however, the entry blood vessel can be any suitable vessel. Moreover, in some embodiments, the inserting can be performed percutaneously.

The retrieval sheath is then advanced through the entry blood vessel and to a target blood vessel, at 54. The target blood vessel can be, for example, the ascending aorta. In other embodiments, however, the target blood vessel can be the descending aorta or any other vessel within the body.

The retrieval sheath is positioned about a proximal end portion of a blood pump from a blood pump assembly, at 56. Referring to FIGS. 9-13, the blood pump assembly includes the blood pump, an expandable member, and a set of struts. The expandable member including a tubular wall in contact an inner surface of the target blood vessel and defining an interior volume. The expandable member includes a set of attachment portions. A first end portion of each strut is coupled to the blood pump, and a second end portion of each strut is coupled to a corresponding attachment portion such that at least a portion of the blood pump is within the interior volume of the expandable member and suspended within the target blood vessel.

An end portion of the retrieval sheath is moved distally relative to the blood pump. At 58. This operation is performed to A) remove the second end portion of each strut from the corresponding attachment portion and B) place the blood pump and the plurality of struts within the retrieval sheath. In some embodiments, movement of the end portion of the retrieval sheath distally relative to the blood pump causes removal of the second end portion of each strut from within a slot defined by the corresponding attachment portion. In some embodiments, movement of the end portion of the retrieval sheath distally relative to the blood pump includes rotating the blood pump and struts relative to the expandable member to "unlock" the struts from the corresponding attachment portion. In some embodiments, movement of the end portion of the retrieval sheath distally relative to the blood pump is accompanied by application of a proximal force to the blood pump to maintain the blood pump relative to the expandable member.

The retrieval sheath, including the blood pump and the plurality of struts, is then retracted from the target blood vessel, at 59.

As described above, in some embodiments, any of the blood pump assemblies can include a self-contained and/or close coupled power supply. In this manner, the assembly can include a power supply (battery, capacitance power supply, etc.) that can be disposed along with the blood pump within the vasculature. The power supply (e.g., the power supply 311) can include any suitable battery of different sizes, made from different material or cell packs. The battery can also be configured to be charged or discharged at slow or fast rate. In some embodiments, the internal power supply includes a re-chargeable battery or an ultra-capacitor. The power supply powers the electronics involved, pump, and other control circuitry for programming of the pump.

In some embodiments, any of the power supplies described herein can include and/or be coupled to a control system at the implant site or outside can perform power management and adjust for sleep mode, idle mode, activation and improved operational mode based on the history of use of the assembly.

Figure 21:
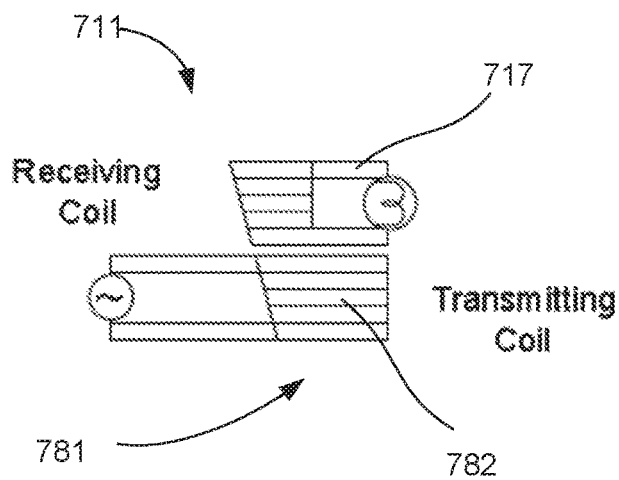
FIGS. 21-23 are schematic illustrations of inductance and resonance technology that can be used with any of the systems described herein, according to an embodiment.
Figure 22:
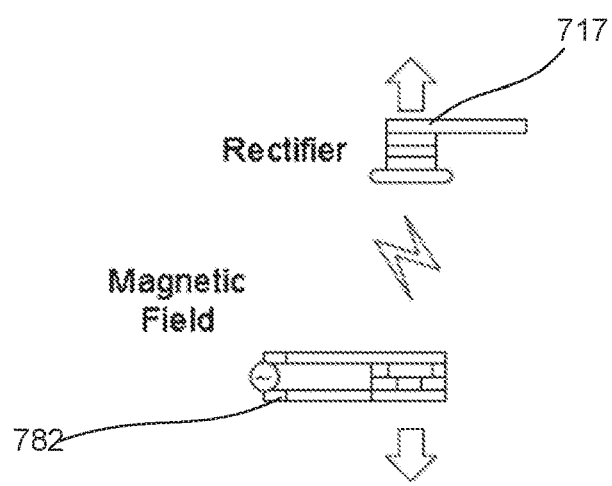
Figure 23:
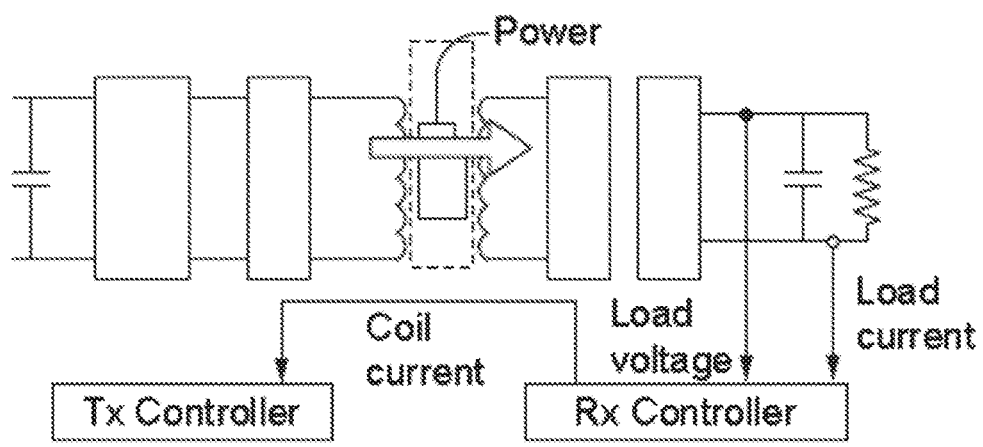

In some embodiments, any of the assemblies described herein can also include an external power source, control system and/or wireless charging system. For example, the external power source (not shown) can be situated in proximity of the subject with implanted blood pump assembly containing the internal power supply. The external power source can be portable and can be placed near the patient within which the blood pump assembly is implanted. In some embodiments, any of the systems described herein can include a wireless power transmission system. The wireless power transmission system may be implemented using any suitable system architecture and resonator design. In some embodiments, the external power supply can charge the internal power supply wirelessly and by means of magnetic resonance as well. For example, FIGS. 21-23 are schematic illustrations of applicable inductance and resonance technology that can be used with any of the systems described herein. Specifically, these figures show a portion of an internal power supply 711 and an external power/charging system 781. Collectively, these systems include a pair of coils that include a receiving coil 717 and a transmitting coil 782. The electromagnetic induction method operates based on the electromagnetic force that arises between coils in the presence of a magnetic flux. As shown in FIG. 22, the magnetic field passes between the receiving coil 717 and the transmitting coil 782. As will be appreciated by those skilled in the art, the receiving coil and transmitting coil can be off axis, as shown. As shown in FIG. 23, power passes from the transmitting coil 782 to the receiving coil 717. In some embodiments, the internal power supply can include a rectifier with a DC converter.

Figure 24:
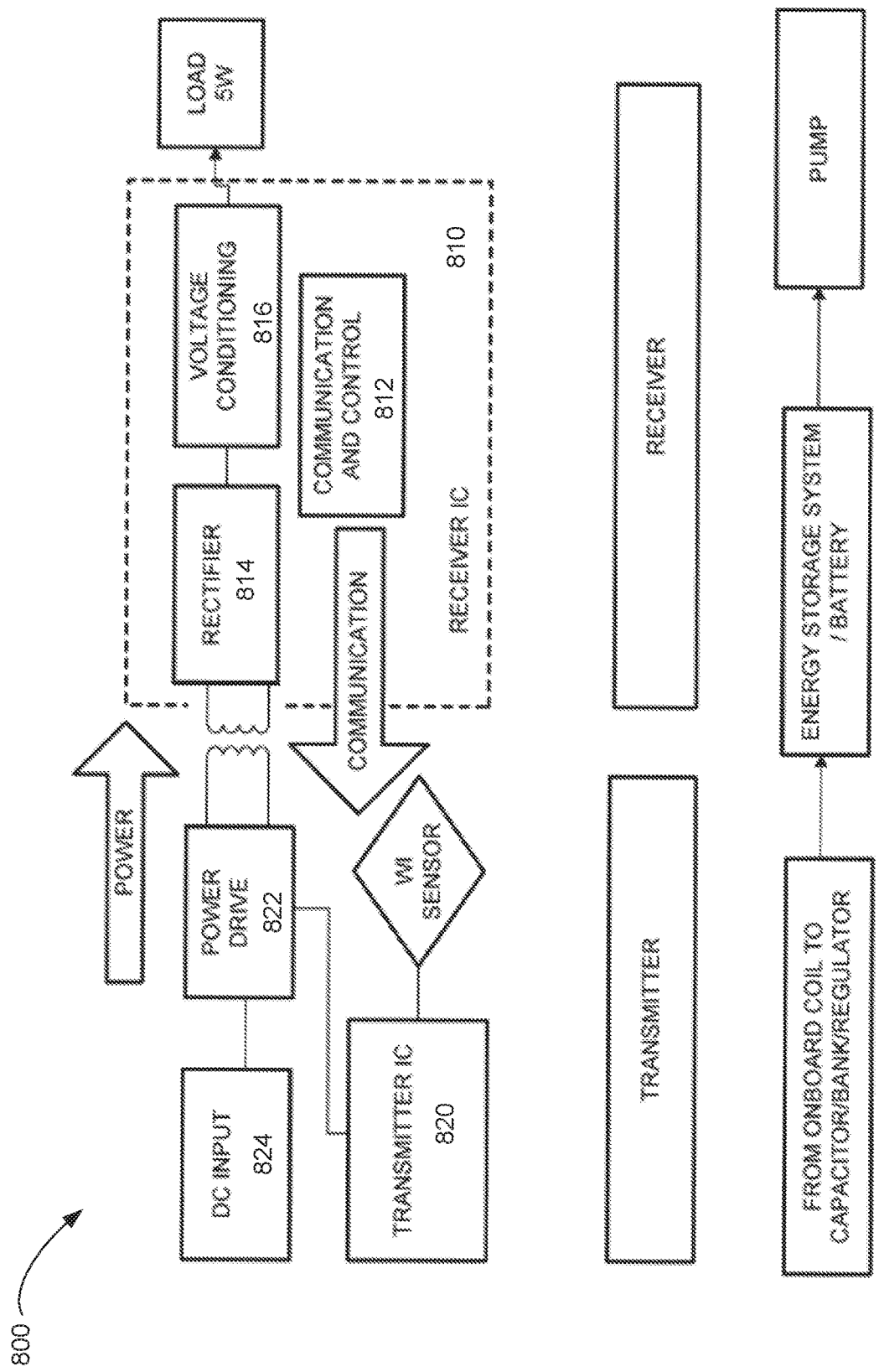
FIG. 24 is a block diagram of a wireless charging system, according to an embodiment, that can be used to power any of the blood pump assemblies described herein.

FIG. 24 is a block diagram of a wireless charging system 800 suitable to power any of the blood pump assemblies described herein. A rectifier IC 810 has a communication module and a controller 812 in communication with a rectifier 814 and a voltage conditioner 816. The rectifier IC 810 is in communication with a transmitter IC 820 that has a power drive 822 and a DC input 824. Power is transmitted from the transmitter IC 820 to the rectifier IC 810. The system can be equipped with a charging system that employs magnetic resonance (resonant inductive coupling). The near field method transmits power wirelessly over a space utilizing resonance phenomena and the transmitter coil and receiver coil oscillates (or resonates) at the same frequency which is determine by the material and shape of the coil. In one configuration, the system uses magnetic induction and n another configuration magnetic resonance.

As will be appreciated by those skilled in the art, the system can operate under relevant standards, e.g. Alliance for Wireless Power (A4WP) for implementation in MI (Q!, WPC, etc.). Energy from the on-board coil is transferred to a capacitor, for example, which is transferred to an energy storage system such as a battery, and then to the implanted vascular pump. The configuration of the system allows for wireless charging. The system described capable of charging multiple implantable devices which have been deployed within the body (e.g., pace maker, pump, defibrillator, etc.). The controller is configured to monitor a fuel gauge or available energy level of the battery by communicating with the implanted system. Based on information provided to the controller, the implanted power supply can begin charging or charge on demand. The controller can be set by the user or the operator to charge on set schedules or based on energy storage level of the implanted power supply.

Figure 25:
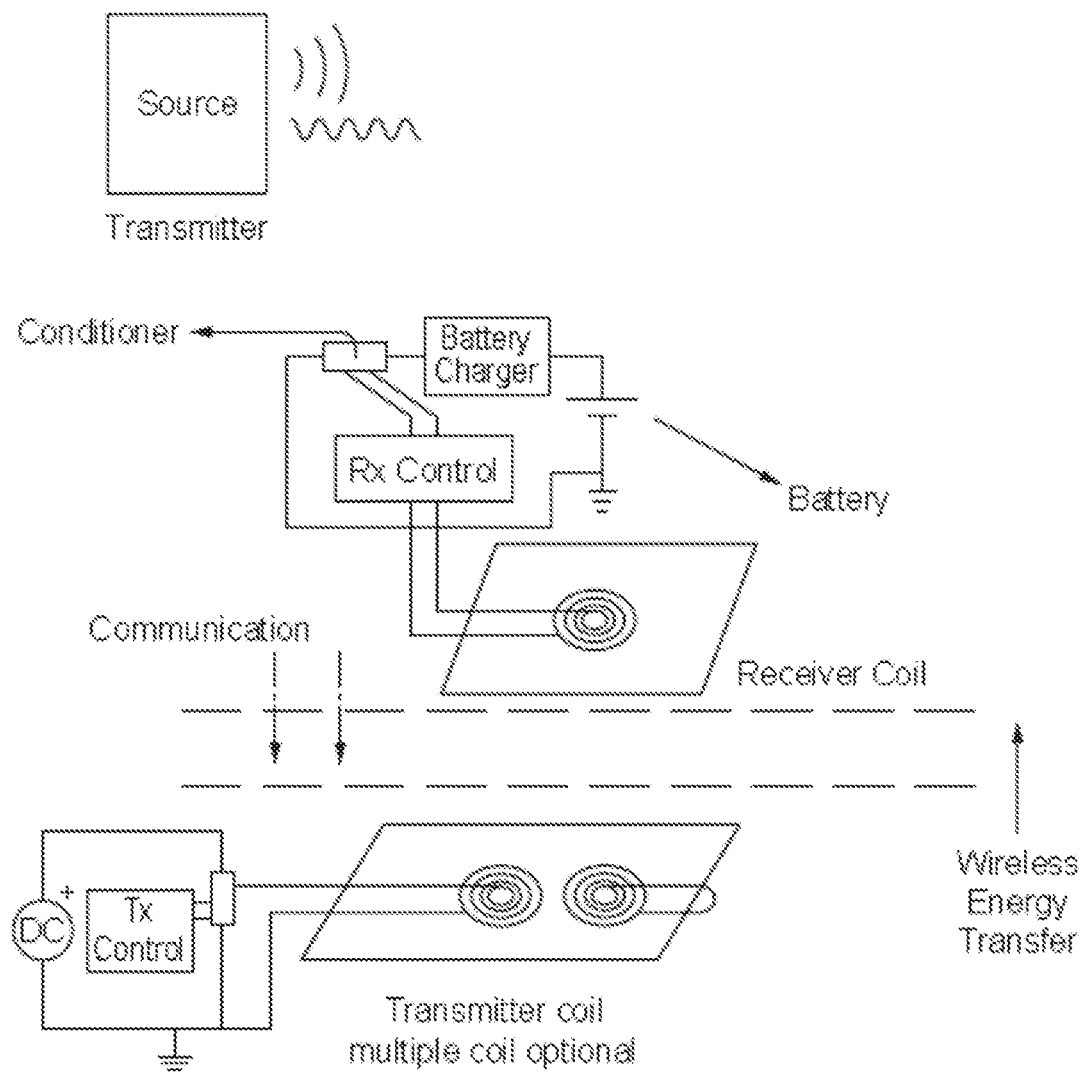
FIG. 25 is a block diagram that illustrates additional details of the wireless charging system shown in FIG. 24.

FIG. 25 is a block diagram that illustrates additional details of the wireless charging system 800. The external system 800 provides for an improved configuration for wireless power transfer for biological applications by use of magnetic resonance, as described herein. In some embodiments, the external system can transmit sufficient power to charge a battery (e.g., the battery contained within the internal power supply, of the types described herein). The magnetic resonance charging can be activated by a user from outside of the body, by a power supply or implanted device signaling the power supply to get activated when the low energy storage level is sensed. To re-charge the power supply for the pump once the pump has been implanted, a wireless charger is brought into proximity to the exterior of the chest wall of a patient. As will be appreciated by those skilled in the art, magnetic resonance charging (or wireless charging) uses an electromagnetic field to transfer energy between two objects as shown in FIGS. 21-25. Energy is conveyed through magnetic resonance coupling to an electrical device, which then uses that energy to charge the device battery.

Although the blood pump assemblies have been shown and described here as including an implanted (also referred to as internal) power supply that is coupled within the target blood vessel, in other embodiments, any of the pump assemblies (and methods) described herein can include an implanted blood pump that is coupled to a power supply implanted within the body, but outside of the heart or the target blood vessel. For example, in some embodiments, the blood pump assembly 100 or 400 (or any other blood pump assemblies described herein) can include a blood pump coupled within the ascending aorta that is electrically coupled to a power supply that is implanted within the body, but outside of the heart, the aorta, or the like. For example, in some embodiments, a blood pump assembly can include a power supply that is superficially mounted (e.g., in a subclavicular region) of the body. In such embodiments, an electrical lead can be routed within the body to couple the blood pump and the power supply.

In some embodiments, such blood pump assemblies can include an electrical lead that is advanced transseptally through the right portion of the heart and into the left ventricle, where it is then coupled to a blood pump implanted within the ascending aorta. The blood pump can be implanted within the ascending aorta in accordance with any of the methods and systems described herein.

Figure 26:
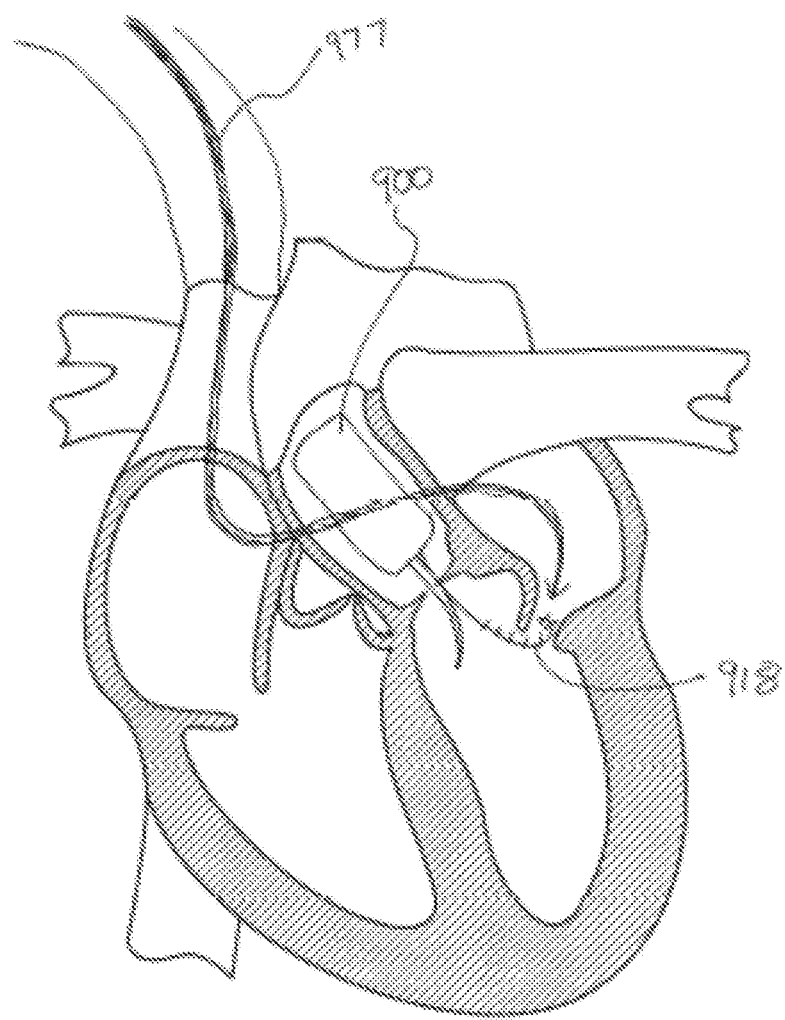
FIG. 26 is a schematic illustration showing a method of retrieving an electrical lead from an intracardiac blood pump assembly, according to an embodiment.
Figure 27:
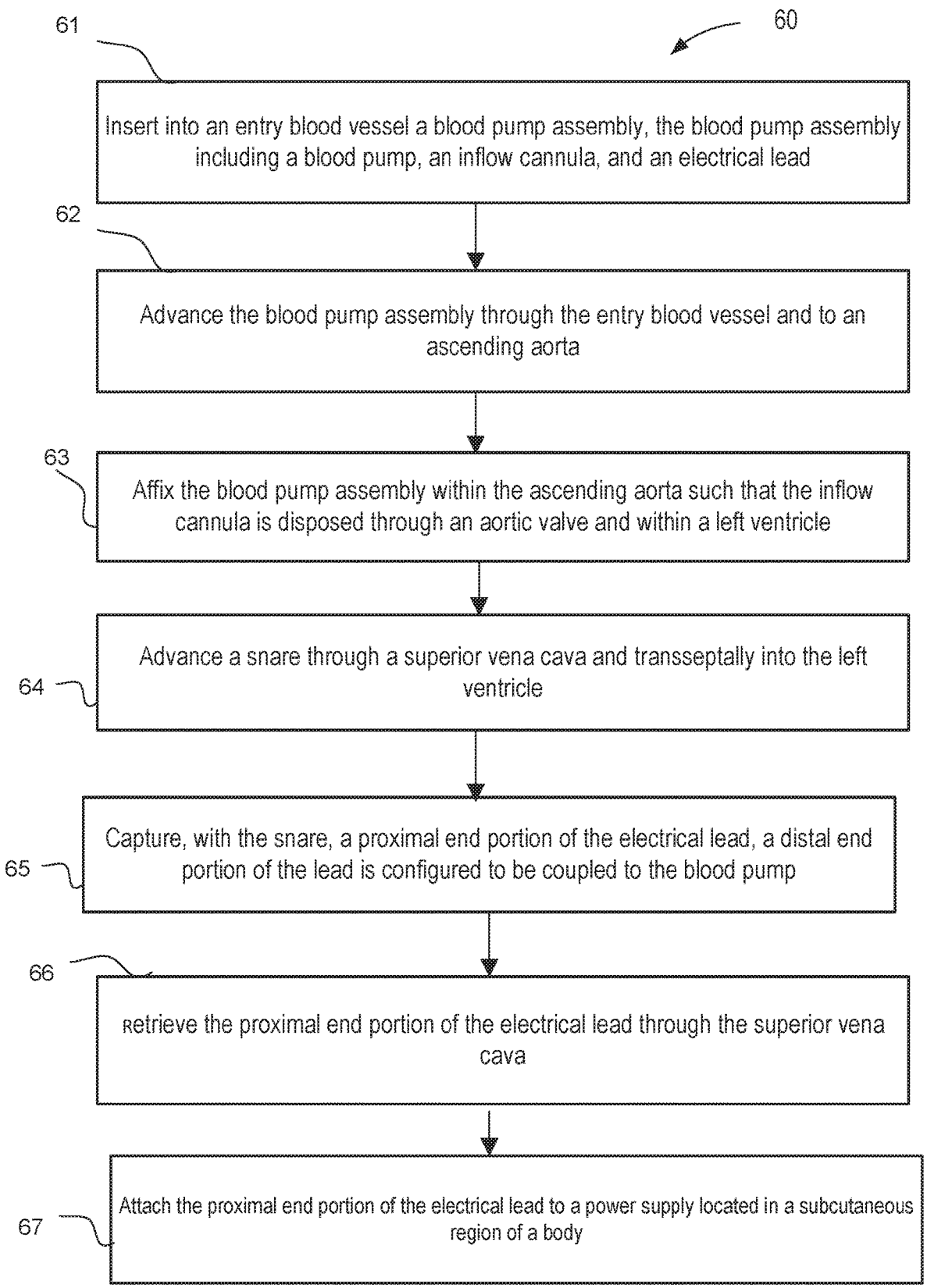
FIG. 27 is a flow chart of a method of retrieving an electrical lead from an intracardiac blood pump assembly, according to an embodiment.

In some embodiments, a method includes routing an electrical lead from a power supply and transseptally into the left side of the heart. For example, FIG. 26 is a schematic illustration of and FIG. 27 is a flow chart illustrating a method 60 of coupling an electrical lead between an implanted extracardiac power supply and an intracardiac pump assembly, according to an embodiment. The method 60 can performed using any of the blood pump assemblies described herein. Although the schematic illustration in FIG. 26 shows a blood pump 901 having an electrical lead 918 that is retrieved using a snare 977, the method can be performed using any of the blood pump assemblies described herein.

The method 60 includes inserting into an entry blood vessel a blood pump assembly, at 61. The blood pump assembly including a blood pump, an inflow cannula, and an electrical lead. The blood pump assembly is then advanced through the entry blood vessel and to an ascending aorta, at 62. The blood pump assembly is affixed within the ascending aorta such that the inflow cannula is disposed through an aortic valve and within a left ventricle, at 63. The implanting and affixing of the blood pump assembly can be performed according to any of the methods described herein. For example, in some embodiments, the method 60 includes implanting and affixing a blood pump assembly that includes an expandable member (not shown in FIG. 26).

A snare is then advanced through a superior vena cava and transseptally into the left ventricle, at 64. This is shown in FIG. 26 by the snare 977, which advances transseptally as shown by the arrow at the end of the snare. A proximal end portion of the electrical lead is then captured using the snare, at 65. As shown in FIG. 26, a distal end portion of the lead is configured to be coupled to the blood pump. The proximal end portion of the electrical lead is then advanced through the superior vena cava, at 66. The method further includes attaching the proximal end portion of the electrical lead to a power supply located in a subcutaneous region of a body, at 67.

Figure 29:
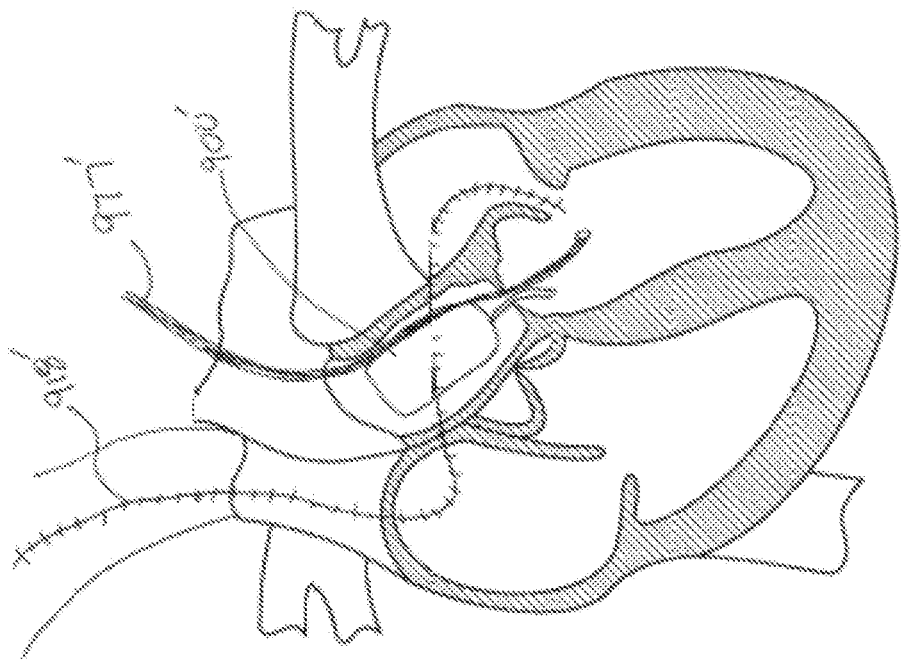
FIGS. 28 and 29 are schematic illustrations showing a method of routing and coupling an electrical lead to an intracardiac blood pump assembly, according to an embodiment.
Figure 28:
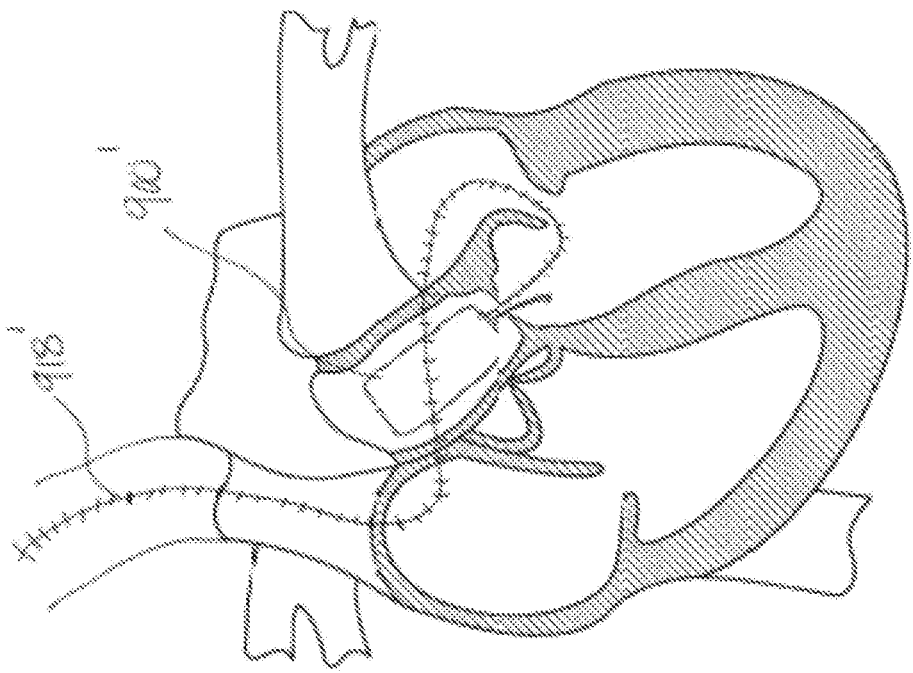
Figure 30:
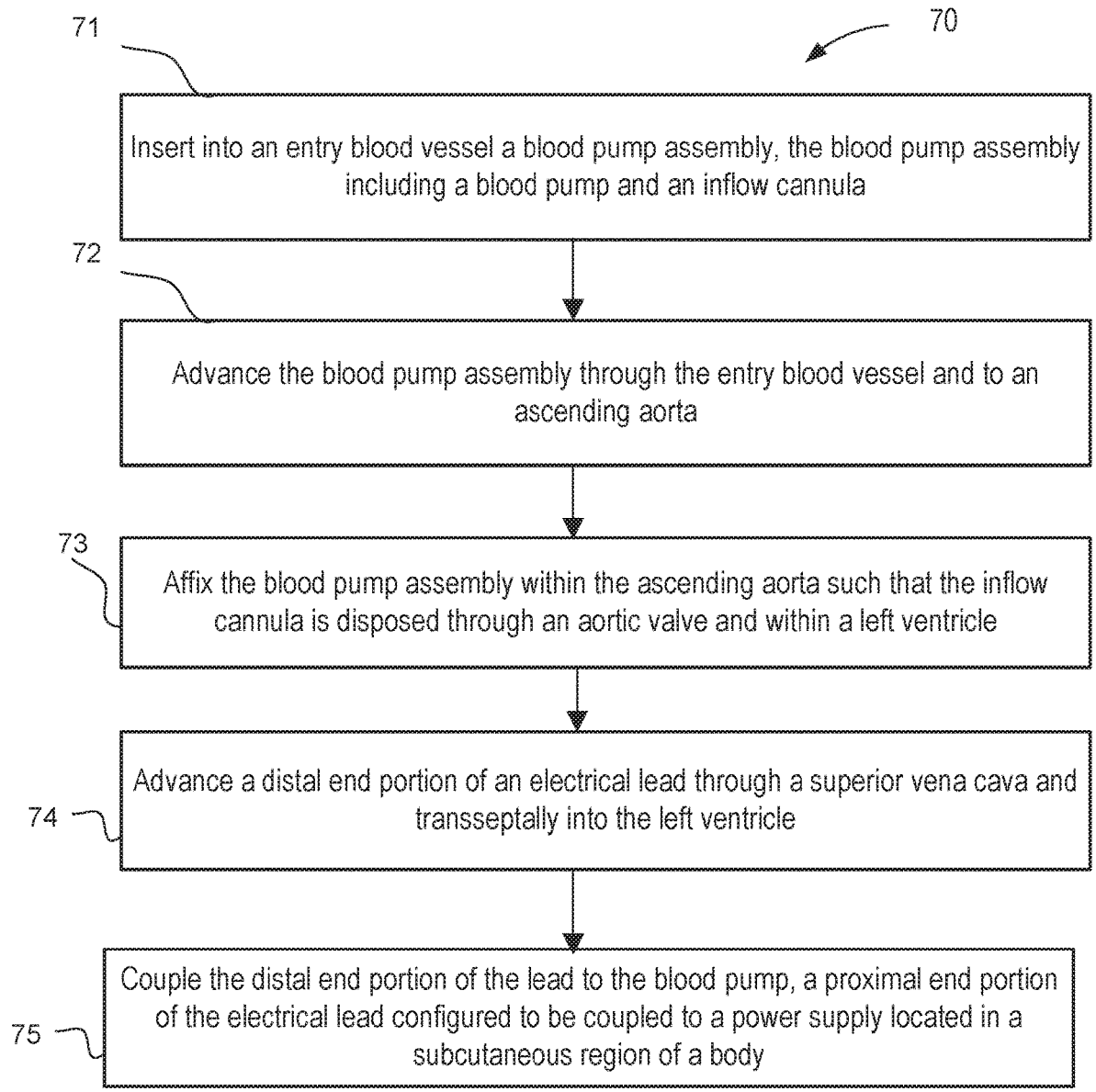
FIG. 30 is a flow chart of a method of routing and coupling an electrical lead to an intracardiac blood pump assembly, according to an embodiment.

Although the method 60 is shown as implanting the pump assembly with the electrical lead attached thereto, and then routing the lead back to the power supply, in other embodiments, the pump assembly can be implanted without the electrical lead, and the lead can be routed transseptally into the left ventricle and then coupled to the pump assembly. For example, FIGS. 28 and 29 are schematic illustrations of and FIG. 30 is a flow chart illustrating a method 70 of coupling an electrical lead between an implanted extracardiac power supply and an intracardiac pump assembly, according to an embodiment. The method 70 can performed using any of the blood pump assemblies described herein. Although the schematic illustration in FIGS. 28 and 29 shows a blood pump 901' having an electrical lead 918' that is manipulated and attached using a snare 977', the method can be performed using any of the blood pump assemblies described herein.

The method 70 includes inserting into an entry blood vessel a blood pump assembly, at 71. The blood pump assembly including a blood pump and an inflow cannula. The blood pump assembly is then advanced through the entry blood vessel and to an ascending aorta, at 72. The blood pump assembly is affixed within the ascending aorta such that the inflow cannula is disposed through an aortic valve and within a left ventricle, at 73. The implanting and affixing of the blood pump assembly can be performed according to any of the methods described herein. For example, in some embodiments, the method 70 includes implanting and affixing a blood pump assembly that includes an expandable member (not shown in FIGS. 28 and 29).

A distal end portion of an electrical lead through a superior vena cava and transseptally into the left ventricle snare is then advanced through a superior vena cava and transseptally into the left ventricle, at 74. The distal end portion of the electrical lead is then coupled to the blood pump, at 75. The proximal end portion of the electrical lead is configured to be coupled to a power supply located in a subcutaneous region of a body.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, in some embodiments, any of the expandable members shown and described herein can include a marker portion (e.g., a marker band) configured to allow the practitioner to visualize the position of the expandable member within the blood vessel. Similarly, in some embodiments, any of the blood pumps, inflow cannulas, and electrical leads described herein can include a marker portion. In the manner, the practitioner can visualize the position of the components of the blood pump assembly to ensure the appropriate placement within the body. The marker portions can include any a radiopaque material, such as platinum.

Although shown and described as including a set of flexible segments, in other embodiments, the expandable member 151 (and any of the expandable members shown and described herein) can be monolithically constructed from a material sheet that is fabricated to include a series of pores, and that can transition from the collapsed configuration to the expanded configuration. For example, in some embodiments, any of the expandable members described herein can be a laser-cut expandable member.

For example, any of the expandable members described herein can be constructed from any suitable material or combination of different materials disclosed herein. Moreover, in some embodiments, at least a portion of any of the expandable members described herein (e.g., the expandable members 151, 251, 351, 451 and 551) can be coated. Such coatings can include, for example, a drug coating.

Any of the blood pump assemblies described herein can include one or more sensors to measure the cardiac output and activity level of the patient. Such sensors can include, for example, a flow sensor, an accelerometer, or the like. Moreover, any of the blood pump assemblies described herein can include a control system configured to receive one or more signals from the sensor(s) and adjust the output of the blood pump based on such signals.

In some embodiments, any of the blood pump assemblies described herein include a close-coupled (or internally mounted) power supply that can be recharged and/or powered by any suitable wireless method, such as, for example, by inductive coupling, capacitive coupling, or the like. Moreover, although the system 800 described above is shown as including one external transmission portion that is coupled to one internal power supply (e.g., within or closely-coupled to the blood pump), in other embodiments, any of the blood pump assemblies or systems described herein can include any number of intermediate structures to facilitate the desired power transfer. For example, in some embodiments, any of the blood pump assemblies described herein can include an external power supply, an internal receiving member (e.g., a pad, harvesting device, or the like) that is subcutaneously mounted, and an internal power supply (e.g., that is within or closely-coupled to the blood pump). In such embodiments, the internal receiving member can be mounted in the subclavicular region, and can be coupled to the power supply of a blood pump mounted within the ascending aorta via an electrical lead. In some embodiments, the electrical lead can be routed to the power supply of the blood pump transseptally according to the method 60 or the method 70 described herein.

Although the blood pump assemblies described herein include a close-coupled (or internally mounted) power supply that can be charged via inductive coupling and a magnetic field, in some embodiments, any of the assemblies described herein can be charged and/or powered via radiofrequency (RF) charging, with the ability to harvest energy by receiving via antenna on the device.

Although various embodiments have been described as having particular features and/or combinations of components, other embodiments are possible having a combination of any features and/or components from any of embodiments where appropriate. For example, any of the expandable members shown and described herein can be constructed from any of the materials described herein with respect to any other expandable member. Specifically, any of the expandable members described herein can be constructed from any suitable material that provides the desired strength, spring characteristics and biocompatibility. For example, in some embodiments, any of the expandable members described herein can be constructed from a metal, such as, for example, a medical grade stainless steel, a cobalt-based alloy, platinum, gold, titanium, tantalum, and/or niobium. In some embodiments, any of the expandable members described herein can be constructed from a shape memory material, such as a nickel-titanium alloy (e.g., Nitinol®). In other embodiments, any of the expandable members described herein) can be constructed from a polymeric material, such as, for example, poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly (glycolide-co-trimethylene carbonate) (PGA/PTMC), polydioxanone (PDS), Polycaprolactone (PCL), polyhydroxybutyrate (PHBT), poly(phosphazene)poly(D,L-lactide-co-caprolactone) PLA/PCL), poly(glycolide-co-caprolactone) (PGA/PCL), poly(phosphate ester), or the like.

Any of the struts described herein can be constructed from any suitable material that provides the desired strength to suspend the blood pump and/or power supply within a blood vessel. Moreover, any of the struts described herein can be flexible and can change their length and/or orientation to allow the expandable member to transition from the collapsed configuration to the expanded configuration. For example, any of the struts described herein can be constructed from a metallic material, such as, a medical grade stainless steel. In other embodiments, any of the struts described herein can be constructed from a shape memory material, such as a nickel-titanium alloy (e.g., Nitinol®). In other embodiments, any of the struts described herein can be constructed from a polymeric material, such as, for example, poly(L-lactide) (PLLA), poly(D,L-lactide) (PLA), poly(glycolide) (PGA), poly(L-lactide-co-D,L-lactide) (PLLA/PLA), polyethylene terephthalate (PET), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester), or the like.

What is claimed is:
1. An apparatus, comprising:
an expandable member configured to transition from a collapsed configuration to an expanded configuration, the expandable member including a plurality of flexible segments that form a tubular wall defining an interior volume, the plurality of flexible segments configured to contact an inner surface of a blood vessel when the expandable member is in the expanded configuration, the expandable member including a plurality of attachment portions;
a blood pump including a housing; and a plurality of struts each having a first end portion fixedly coupled to the housing, each strut from the plurality of struts having a second end portion configured to be removably coupled to a corresponding attachment portion from the plurality of attachment portions such that the blood pump can be removably coupled to the expandable member with at least a portion of the housing disposed within the interior volume of the expandable member.

2. The apparatus of claim 1, wherein the second end portion of a strut from the plurality of struts is configured to be slidingly disposed within a slot defined by an attachment portion from the plurality of attachment portions.

3. The apparatus of claim 2, wherein the attachment portion from the plurality of attachment portions includes a shoulder configured to limit movement of the second end portion of the strut from the plurality of struts in a first direction when the second end portion is disposed within the slot defined by the attachment portion, the second end portion of the strut from the plurality of struts configured to move in a second direction within the slot to remove the second end portion from the attachment portion.

4. The apparatus of claim 1, wherein the second end portion of a strut from the plurality of struts defines a slot within which a protrusion of an attachment portion from the plurality of attachment portions is configured to be slidingly disposed.

5. The apparatus of claim 1, wherein at least one of the second end portion of a strut from the plurality of struts or an attachment portion from the plurality of attachment portions includes a detent.

6. The apparatus of claim 1, wherein:
the second end portion of a strut from the plurality of struts includes a protrusion having a longitudinal centerline that is offset from a centerline of the strut; and
an attachment portion from the plurality of attachment portions defines a slot within which the protrusion is configured to be slidingly disposed, the attachment portion including a shoulder configured to prevent movement of the protrusion with the slot in a first direction, the attachment portion including a detent configured to resist movement of the protrusion within the slot in a second direction.

7. The apparatus of claim 1, wherein the tubular wall and the plurality of attachment portions define a continuous inner surface defining the interior volume.

8. The apparatus of claim 1, wherein a longitudinal center line of each strut from the plurality of struts forms an acute angle with a longitudinal axis of the blood pump.

9. The apparatus of claim 1, wherein the plurality of flexible segments is configured to contact the inner surface of the blood vessel along a length at least one quarter a length of the housing of the blood pump.

10. The apparatus of claim 1, wherein the plurality of struts is configured to suspend the blood pump within the blood vessel spaced apart from the inner surface of the blood vessel, the apparatus further comprising:
a power supply coupled to the blood pump, the power supply configured to be suspended within the blood vessel spaced apart from the inner surface of the blood vessel.

11. The apparatus of claim 1, wherein the expandable member is a first expandable member, the plurality of struts is a first plurality of struts configured to suspend the blood pump within the blood vessel spaced apart from the inner surface, the apparatus further comprising:

a second expandable member including a second plurality of flexible segments that form a second tubular wall defining a second interior volume, the second plurality of flexible segments configured to contact the inner surface of a blood vessel when the second expandable member is in an expanded position, the expandable member including a second plurality of attachment portions;
a power supply coupled to the blood pump; and
a second plurality of struts each having a first end portion coupled to the power supply, each strut from the second plurality of struts having a second end portion configured to be removably coupled to a corresponding attachment portion from the second plurality of attachment portions such that at least a portion of the power supply can be removably suspended within the blood vessel spaced apart from the inner surface of the blood vessel.

12. The apparatus of claim 1, wherein the first end portion of each strut is fixedly coupled to the housing by a weld, an adhesive, an attachment band, a pin joint or a ball joint.

13. An apparatus, comprising:
an expandable member configured to transition from a collapsed configuration to an expanded configuration, the expandable member including a plurality of flexible segments that form a tubular wall defining an interior volume, the plurality of flexible segments configured to contact an inner surface of a blood vessel when the expandable member is in the expanded configuration, the expandable member including a plurality of attachment portions;
a blood pump;
a power supply coupled to the blood pump and configured to provide power to drive the blood pump; and
a plurality of struts each having a first end portion fixedly coupled to at least one of the blood pump or the power supply, each strut from the plurality of struts having a second end portion configured to be removably coupled to a corresponding attachment portion from the plurality of attachment portions such that the blood pump and the power supply can be removably coupled to the expandable member with at least one of a portion of the blood pump or a portion of the power supply disposed within the interior volume of the expandable member.

14. The apparatus of claim 13, wherein the blood pump and the power supply are contained within a monolithically-constructed housing.

15. The apparatus of claim 13, wherein:
the blood pump includes a housing, the first end portion of each strut from the plurality of struts is coupled to the housing; and
the power supply is disposed outside of the housing and is coupled to the blood pump by a flexible lead.

16. The apparatus of claim 13, wherein the power supply includes an energy storage member and a receiving coil, the receiving coil configured to be electromagnetically coupled to a power transmission coil such that power can be transmitted wirelessly to the energy storage member via the receiving coil from an external power supply outside of a body when the power supply is disposed within the blood vessel.

17. The apparatus of claim 13, wherein the expandable member is a first expandable member, the plurality of struts is a first plurality of struts configured to suspend the blood pump within the blood vessel spaced apart from the inner surface, the first end portion of each strut from the first plurality of struts is coupled to the blood pump, the apparatus further comprising:
- a second expandable member including a second plurality of flexible segments that form a second tubular wall defining a second interior volume, the second plurality of flexible segments configured to contact the inner surface of a blood vessel when the second expandable member is in an expanded position, the expandable member including a second plurality of attachment portions; and
- a second plurality of struts each having a first end portion coupled to the power supply, each strut from the second plurality of struts having a second end portion configured to be removably coupled to a corresponding attachment portion from the second plurality of attachment portions such that at least a portion of the power supply can be removably suspended within the blood vessel spaced apart from the inner surface of the blood vessel.

18. The apparatus of claim 17, wherein:
the blood pump includes a housing, the first end portion of each strut from the first plurality of struts is coupled to the housing; and
the power supply is disposed outside of the housing and is coupled to the blood pump by a flexible lead.

19. The apparatus of claim 13, wherein the first end portion of each strut is fixedly coupled to the housing by a weld, an adhesive, an attachment band, a pin joint or a ball joint.

20. A method, comprising:
inserting into an entry blood vessel a blood pump assembly, the blood pump assembly including a blood pump, an expandable member, and a plurality of struts, the expandable member including a plurality of flexible segments that form a tubular wall defining an interior volume, the expandable member including a plurality of attachment portions, a first end portion of each strut from the plurality of struts fixedly coupled to the blood pump, a second end portion of each strut from the plurality of struts removably coupled to a corresponding attachment portion from the plurality of attachment portions such that at least a portion of the blood pump is within the interior volume of the expandable member, the inserting performed when the expandable member is in a collapsed configuration;
advancing the blood pump assembly through the entry blood vessel and to a target blood vessel; and
transitioning the expandable member from the collapsed configuration to an expanded configuration such that the plurality of flexible segments contact an inner surface of the target blood vessel and the blood pump is suspended within the target blood vessel by the plurality of struts, the blood pump and the plurality of struts configured to be removed from the target blood vessel by removing the second end portion of each strut from the plurality of struts from the corresponding attachment portion.

21. The method of claim 20, wherein the inserting includes percutaneously inserting a catheter containing the blood pump assembly into the entry blood vessel.

22. The method of claim 21, wherein:
the entry blood vessel is a femoral artery; and
the target blood vessel is an ascending aorta.

23. The method of claim 20, wherein the blood pump assembly includes a power supply coupled to the blood pump and configured to provide power to drive the blood pump.

24. The method of claim 23, wherein the expandable member is a first expandable member, the plurality of struts is a first plurality of struts, the first end portion of each strut from the first plurality of struts is coupled to the blood pump to suspended the blood pump within the target blood vessel, and the blood pump assembly includes a second expandable member and a second plurality of struts, the second expandable member including a second plurality of flexible segments that form a second tubular wall defining a second interior volume, the second expandable member including a second plurality of attachment portions, a first end portion of each strut from the second plurality of struts coupled to the power supply, a second end portion of each strut from the plurality of struts removably coupled to a corresponding attachment portion from the second plurality of attachment portions such that at least a portion of the power supply is within the interior volume of the second expandable member, the method further comprising:
transitioning the second expandable member to its expanded configuration such that the second plurality of flexible segments contact the inner surface of the target blood vessel and the power supply is suspended within the target blood vessel by the second plurality of struts, the power supply and the second plurality of struts configured to be removed from the target blood vessel by removing the second end portion of each strut from the second plurality of struts from the corresponding attachment portion from the second plurality of attachment portions.

25. The method of claim 20, wherein each strut from the plurality of struts is fixedly coupled to the blood pump a weld, an adhesive, an attachment band, a pin joint or a ball joint.

* * * * *

UNITED STATES PATENT AND TRADEMARK OFFICE
CERTIFICATE OF CORRECTION

| | | |
|---|---|---|
| PATENT NO. | : 11,406,812 B2 | Page 1 of 1 |
| APPLICATION NO. | : 16/087079 | |
| DATED | : August 9, 2022 | |
| INVENTOR(S) | : Ramtin Agah et al. | |

It is certified that error appears in the above-identified patent and that said Letters Patent is hereby corrected as shown below:

On the Title Page

Applicants item (71): delete "Kamran Najmabadi, Palo Alto, CA (US)"

Signed and Sealed this
Eighth Day of November, 2022

Katherine Kelly Vidal
*Director of the United States Patent and Trademark Office*